(12) United States Patent
Muro-Galindo et al.

(10) Patent No.: US 9,707,299 B2
(45) Date of Patent: Jul. 18, 2017

(54) TARGETED CARRIERS FOR INTRACELLULAR DRUG DELIVERY

(75) Inventors: Silvia Muro-Galindo, Silver Spring, MD (US); Vladimir R. Muzykantov, Warminster, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 874 days.

(21) Appl. No.: 12/600,947

(22) PCT Filed: May 22, 2008

(86) PCT No.: PCT/US2008/006589
§ 371 (c)(1),
(2), (4) Date: Nov. 19, 2009

(87) PCT Pub. No.: WO2008/147526
PCT Pub. Date: Dec. 4, 2008

(65) Prior Publication Data
US 2010/0151005 A1    Jun. 17, 2010

Related U.S. Application Data

(60) Provisional application No. 60/931,552, filed on May 23, 2007.

(51) Int. Cl.
A61K 9/50 (2006.01)
A61K 9/14 (2006.01)
A61K 47/48 (2006.01)

(52) U.S. Cl.
CPC .. *A61K 47/48223* (2013.01); *A61K 47/48092* (2013.01); *A61K 47/48561* (2013.01); *A61K 47/48853* (2013.01)

(58) Field of Classification Search
None
See application file for complete search history.

(56) References Cited

U.S. PATENT DOCUMENTS

| | | |
|---|---|---|
| 5,175,270 A | 12/1992 | Nilsen |
| 5,653,979 A | 8/1997 | Muzykantov |
| 6,274,723 B1 | 8/2001 | Nilsen |
| 6,488,927 B2 | 12/2002 | Muzykantov |
| 6,822,086 B1 | 11/2004 | Papisov |
| 7,041,287 B2 | 5/2006 | Muzykantov |
| 7,157,087 B2 | 1/2007 | Muzykantov |
| 7,172,760 B2 | 2/2007 | Muzykantov |
| 7,674,466 B2 | 3/2010 | Muzykantov |
| 2002/0072060 A1 | 6/2002 | Getts |
| 2004/0157330 A1 | 8/2004 | Sheridan |
| 2004/0220084 A1 | 11/2004 | Sandhu |
| 2005/0089890 A1* | 4/2005 | Cubicciotti ............ 435/6 |
| 2005/0130180 A1 | 6/2005 | Luo |
| 2005/0281845 A1 | 12/2005 | Bachmann |
| 2006/0040879 A1* | 2/2006 | Kosak ............... 514/44 |
| 2007/0065451 A1 | 3/2007 | Muzykantov |
| 2008/0050389 A1 | 2/2008 | Muzykantov |
| 2009/0130104 A1 | 5/2009 | Muzykantov |

FOREIGN PATENT DOCUMENTS

| | | |
|---|---|---|
| WO | WO 96/30047 | 10/1996 |
| WO | WO 99/45960 | 9/1999 |
| WO | WO 99/59611 | 11/1999 |
| WO | WO 00/07625 | 2/2000 |
| WO | WO 2008/039206 | 4/2008 |
| WO | WO 2009/086552 | 7/2009 |
| WO | WO 2010/045518 | 4/2010 |

OTHER PUBLICATIONS

International Preliminary Report on Patentability dated Nov. 24, 2009 in International Patent Application No. PCT/US2008/006589.
International Search Report dated Aug. 8, 2008 in International Patent Application No. PCT/US2008/006589.
Almenar-Queralt et al, Apical topography and modulation of ICAM-1 expression on activated endothelium, American Journal of Pathology, 147(5):1278-88 (Nov. 2005).
Andrews et al, Phagolysosomal escape by intracellular pathogens, Parasitology Today, 7(12):335-340 (Dec. 1991).
Bonazzi et al, Bacterial entry into cells: a role for the endocytic machinery, FEBS Letters, 580(12):2962-7 (May 2006).
Borucki et al, Suspension microarray with dendrimer signal amplification allows direct and high-throughput subtyping of Listeria monocytogenes from genomic DNA, Journal of Clinical Microbiology, 43(7):3255-9 (Jul. 2005).
Campbell et al, Gene therapy progress and prospects: viral trafficking during infection, Gene Therapy, 12(18):1353-9 (Sep. 2005).
Choi et al, Temperature-sensitive pluronic/poly(ethylenimine) nanocapsules for thermally triggered disruption of intracellular endosomal compartment, Biomacromolecules, 7(6):1864-70 (Jun. 2006).
Conner et al, Regulated portals of entry into the cell, Nature, 422(6927):37-44 (Mar. 2003).
Cossart et al, Bacterial invasion: the paradigms of enteroinvasive pathogens, Science, 304(5668):242-8 (Apr. 2004).
Diamond et al, Binding of the integrin Mac-1 (CD11b/CD18) to the third immunoglobulin-like domain of ICAM-1 (CD54) and its regulation by glycosylation, Cell, 65(6):961-71 (Jun. 1991).
Dincer et al, Intelligent polymers as nonviral vectors, Gene Therapy, 12 (Suppl 1):S139-45 (Oct. 2005).
Fuchs et al, Acidification and ion permeabilities of highly purified rat liver endosomes, Journal Biological Chemistry, 264(4):2212-20 (Feb. 1989).
Kakudo et al, Transferrin-modified liposomes equipped with a pH-sensitive fusogenic peptide: an artificial viral-like delivery system, Biochemistry, 43(19):5618-28 (May 2004).
Killisch et al, Characterization of early and late endocytic compartments of the transferrin cycle. Transferrin receptor antibody blocks erythroid differentiation by trapping the receptor in the early endosome, Journal of Cell Science, 103(Pt 1):211-232 (Sep. 1992).

(Continued)

*Primary Examiner* — Doug Schultz
(74) *Attorney, Agent, or Firm* — Howson & Howson LLP

(57) ABSTRACT

The invention provides a method for delivering a cargo molecule into a cell using a targeted DNA-based carrier (e.g., DNA dendrimer). Compositions and kits useful in the practice of the methods are also provided.

15 Claims, 13 Drawing Sheets

(56) References Cited

OTHER PUBLICATIONS

Li et al, Controlled assembly of dendrimer-like DNA, Nature Materials, 3(1):38-42 (Jan. 2004).
Li et al, Multiplexed detection of pathogen DNA with DNA-based fluorescence nanobarcodes, Nature Biotechnology, 23(7):885-9 (Jul. 2005).
Lowe et al, Multiplexed, particle-based detection of DNA using flow cytometry with 3DNA dendrimers for signal amplification, Cytometry A, 60(2):135-44 (Aug. 2004).
Magzoub et al, Modeling the endosomal escape of cell-penetrating peptides: transmembrane pH gradient driven translocation across phospholipid bilayers, Biochemistry, 44(45):14890-7 (Nov. 2005).
Melikov et al, Arginine-rich cell penetrating peptides: from endosomal uptake to nuclear delivery, Cellular and Molelecular Life Sciences, 62(23):2739-49 (Dec. 2005).
Mellman, The importance of being acid: the role of acidification in intracellular membrane traffic, Journal of Experimental Biology, 172:39-45 (Nov. 1992).
Mora et al, Dendrimer FISH detection of single-copy intervals in acute promyelocytic leukemia, Molecular and Cellular Probes, 20(2):114-20 (Apr. 2006).
Murciano et al, ICAM-directed vascular immunotargeting of antithrombotic agents to the endothelial luminal surface, Blood, 101(10):3977-3984 (May 2003).
Muro et al, A novel endocytic pathway induced by clustering endothelial ICAM-1 or PECAM-1, Journal of Cell Science, 116(Pt 8):1599-609 (Apr. 2003).
Muro et al, Control of intracellular trafficking of ICAM-1-targeted nanocarriers by endothelial Na+/H+ exchanger proteins, American Journal of Physiology. Lung Cellular and Molecular Physiology, 290(5):L809-17 (May 2006).
Muro et al, Endothelial endocytic pathways: gates for vascular drug delivery, Current Vascular Pharmacology, 2(3):281-299 (Jul. 2004).
Muro et al, ICAM-1 recycling in endothelial cells: a novel pathway for sustained intracellular delivery and prolonged effects of drugs, Blood, 105(2):650-8 (Jan. 2005).
Muro et al, Lysosomal enzyme delivery by ICAM-1-targeted nanocarriers bypassing glycosylation- and clathrin-dependent endocytosis, Molecular Therapy, 13(1):135-41 (Jan. 2006).
Muro et al, Slow intracellular trafficking of catalase nanoparticles targeted to ICAM-1 protects endothelial cells from oxidative stress, American Journal of Physiology. Cell Physiology, 285(5):C1339-47 (Nov. 2003).
Muzykantov, Biomedical aspects of targeted delivery of drugs to pulmonary endothelium, Expert Opinion Drug Delivery, 2:909-26 (Sep. 2005).
Newman and Albelda, Cellular and molecular aspects of PECAM-1, Nouvelle Revue Francaise d'Hematologie, 32(Suppl):S9-13 (1992).
Nilsen et al, Dendritic nucleic acid structures, Journal of Theoretical Biology, 187:273-284 (Jul. 1997).
Oh et al, Subtractive proteomic mapping of the endothelial surface in lung and solid tumours for tissue-specific therapy, Nature 429(6992):629-35 (Jun. 2004).
Oishi et al, pH-responsive three-layered PEGylated polyplex micelle based on a lactosylated ABC triblock copolymer as a targetable and endosome-disruptive nonviral gene vector, Bioconjugate Chemistry, 17(3):677-88 (May-Jun. 2006).
Reizman et al, Molecular mechanisms of endocytosis, Cell, 91(6):731-8 (Dec. 1997).
Seligmann et al, Heavy chain diseases: current findings and concepts, immunological Reviews, 48:145-167 (1979).
Singh et al, On the gene delivery efficacies of pH-sensitive cationic lipids via endosomal protonation: a chemical biology investigation, Chemistry & Biology, 11(5):713-23 (May 2004).
Springer, Traffic signals for lymphocyte recirculation and leukocyte emigration: the multistep paradigm, Cell, 76(2):301-314 (Jan. 1994).
Stayton et al, 'Smart' delivery systems for biomolecular therapeutics, Orthodontics and Craniofacial Research, 8(3):219-25 (Aug. 2005).
Suk et al, Gene delivery to differentiated neurotypic cells with RGD and HIV Tat peptide functionalized polymeric nanoparticles, Biomaterials, 27(29):5143-50 (Oct. 2006).
Ward et al, Binding activities of a repertoire of single immunoglobulin variable domains secreted from *Escherichia coli*, Nature, 341:544-546 (Oct. 1989).
Warnock, Regulation of endosomal acidification via Gi-type protein, Kidney International, 55(6):2376-82 (Jun. 1999).
Yessine et al, Membrane-destabilizing polyanions: interaction with lipid bilayers and endosomal escape of biomacromolecules, Advanced Drug Delivery Review, 56(7):999-1021 (Apr. 2004).
Zuhorn et al, Nonbilayer phase of lipoplex-membrane mixture determines endosomal escape of genetic cargo and transfection efficiency, Molecular Therapy, 11(5):801-10 (May 2005).
Examination report issued in corresponding Australian Patent Application No. 2008257419 on Oct. 10, 2012.
Kadushin et al, Enhancement of sensitivity in Luminex dendrimer assays via dendrimer dependent signal amplification, Internet Citation, 2005, p. 1-24, retrieved from Internet: URL: http://www.genisphere.com/pdf/Genisphere_Luminex_Planet_xMAP_042505.pdf.
Genisphere, An introduction to 3DNA technology, Internet Citation, 2005, retrieved from Internet: URL: http://www.genisphere.com.
Extended European Search Report issued in corresponding EP Patent Application No. 08754678.4 on Dec. 12, 2012.

* cited by examiner

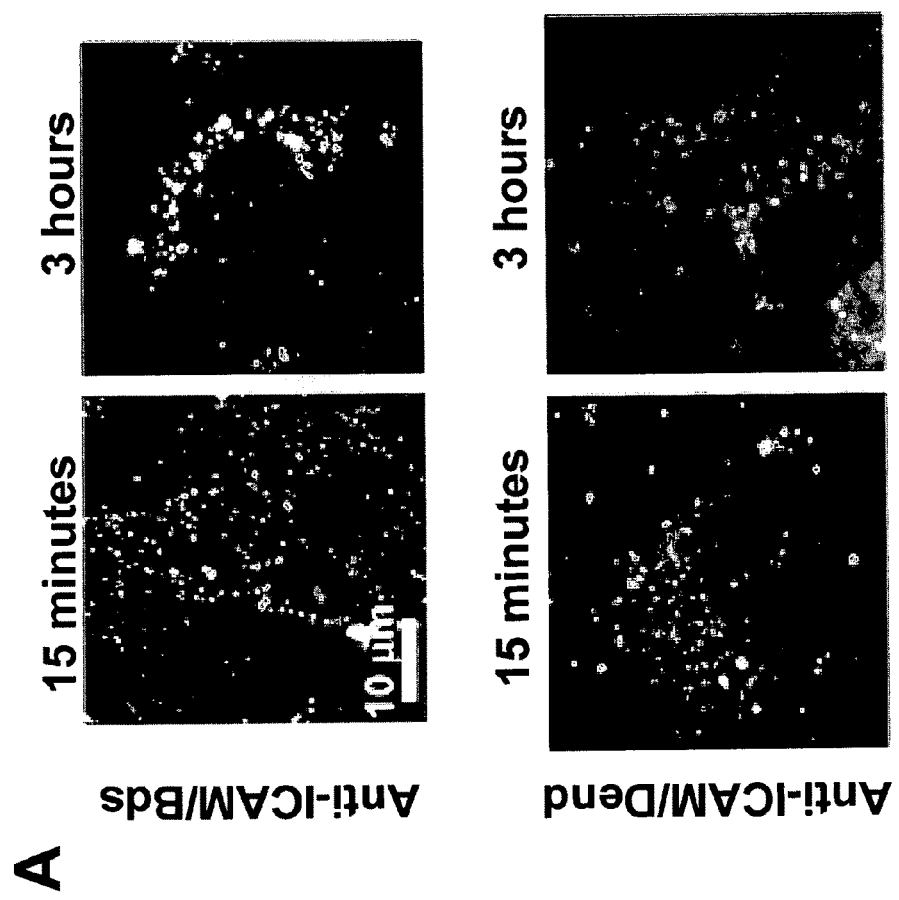

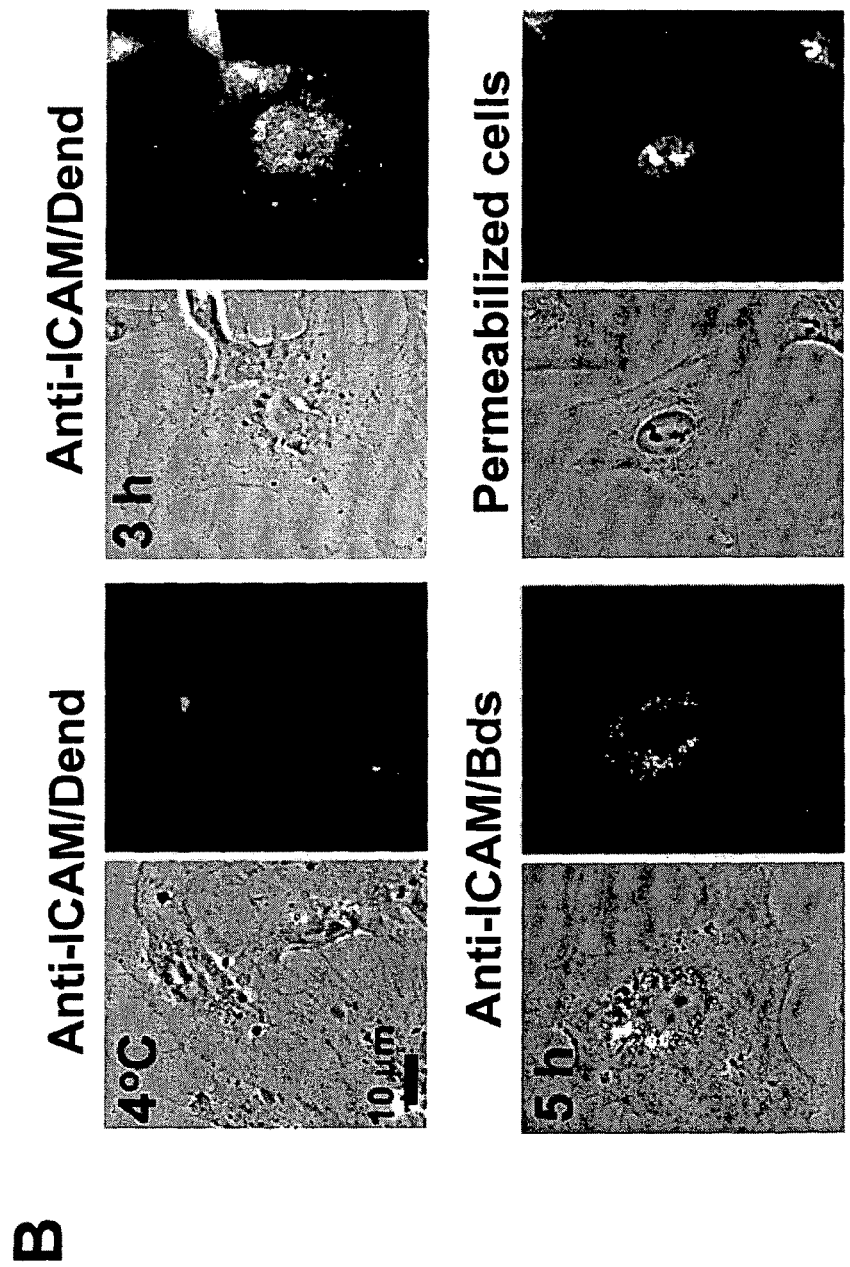

Figure 5A
A Anti-ICAM/Dend
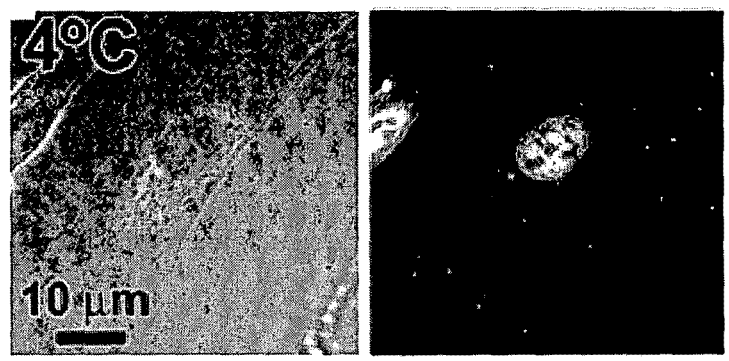
Anti-ICAM/Dend
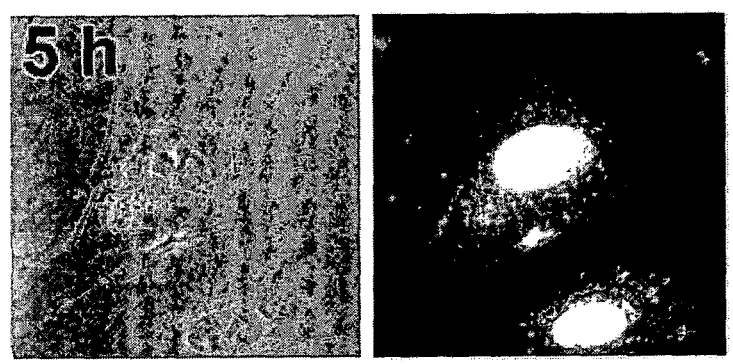
Permeabilized
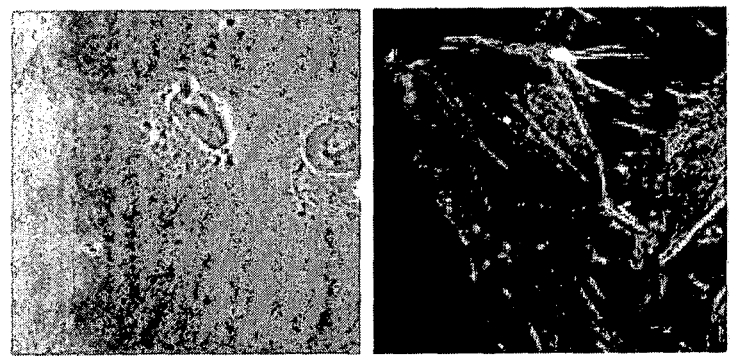

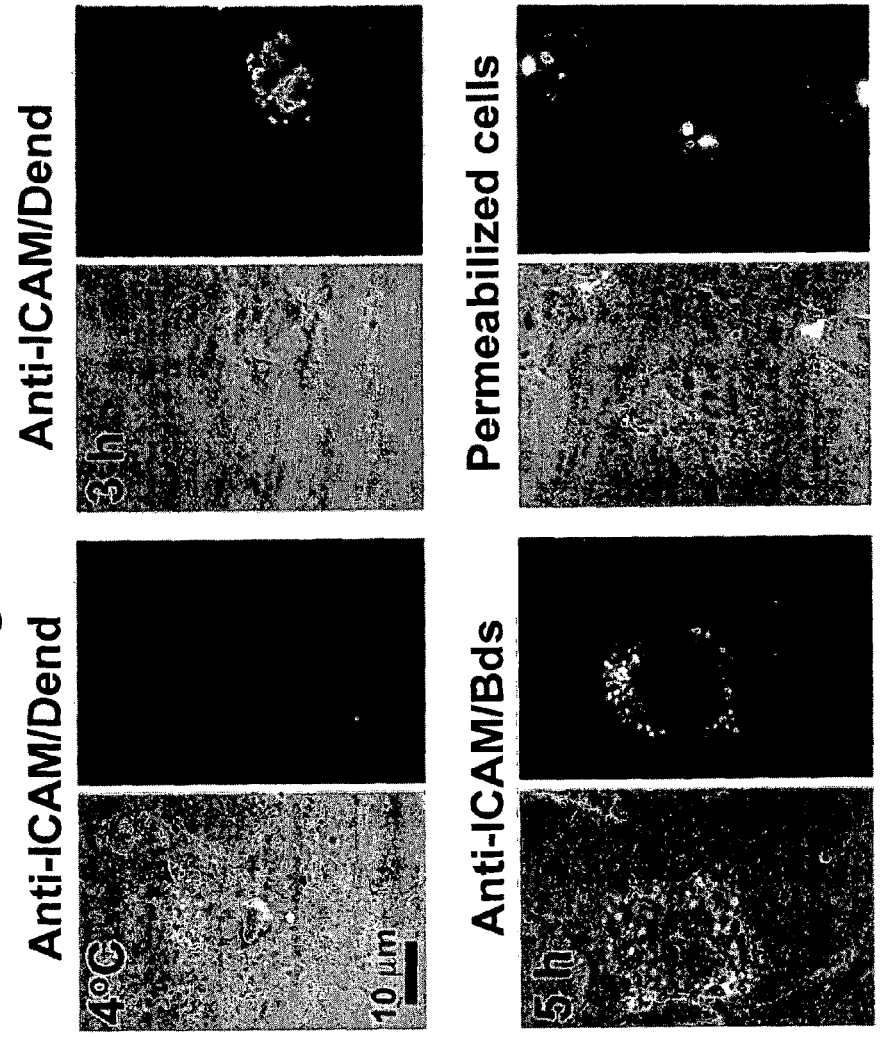

TARGETED CARRIERS FOR INTRACELLULAR DRUG DELIVERY

CROSS-REFERENCE TO OTHER APPLICATIONS

This application is a U.S. national stage of international patent application No. PCT/US2008/006589, filed May 22, 2008, which claims the benefit of the priority of U.S. provisional patent application No. 60/931,552, filed May 23, 2007. Both the international and provisional patent applications are incorporated herein by reference.

BACKGROUND OF THE INVENTION

In many research, diagnostic and therapeutic applications, the targets of action of a molecule, such as a reporter probe, a small molecule drug, a peptide or a nucleic acid, are intracellular. However, targeting of a molecule to selected cell types, achieving intracellular delivery to the cytosol and subsequent trafficking to the desired intracellular compartments represent challenging and elusive goals.

Significant progress in identification of cellular surface determinants, both those relatively selective for certain cell types and those that are characteristic of several or many cell types in the body, has been achieved using techniques including phage display libraries and monoclonal antibodies (Muzykantov, 2005, Expert Opinion Drug Delivery 2:909-26; Oh et al., 2004, Nature 429(6992):629-35). However, the feasibility of using these newly-identified determinants for drug delivery in humans remains to be tested. The functions of many cell surface determinants defined by these modern techniques are either not known or are responsible for vital physiological processes in the body. Thus, inadvertent intervention into or blocking of their functions may lead to harmful side effects.

Internalization of therapeutics or other molecules targeted to cells using these determinants occurs either via passive or receptor-mediated endocytosis. This endocytic internalization can be mediated by common classical endocytic pathways (e.g., clathrin- and caveolar-mediated endocytosis, macropinocytosis and phagocytosis) or by less common non-classical endocytic mechanisms (Mellman, 1992, J Exp Biol 172:39-45; Kornfeld et al., 1989, J Biol Chem 264(4): 2212-20; Muro et al., 2004, Curr Vasc Pharmacol. 2(3):281-99; Riezman et al., 1997, Cell 91(6):731-8; Conner et al., 2003, Nature 422(6927):37-44). Both classical and non-classical pathways typically result in accumulation, and often degradation, of the internalized compounds in endo-lysosomal vesicles (Muro et al., 2004, Curr Vasc Pharmacol. 2(3):281-99; Riezman et al., 1997, Cell 91(6):731-8; Conner et al., 2003, Nature 422(6927):37-44).

Initially, internalized compounds traffic to early endosomes, where combined actions of $H^+$-ATPases, $Na^+$, $K^+$-ATPases, and $Na^+/H^+$-exchangers (Fuchs et al., 1989, J Biol Chem 264(4):2212-20) regulate the pH to values in the interval of 6.3 to 6.5, favoring the separation of the internalized molecules from their cell receptors (Warnock, 1999, Kidney Int. 55(6):2524-5). Internalized materials then traffic to late endosomes, which have a pH around 5 to 5.5 (Mellman, 1992, J Exp Biol 172:39-45; Killisch et al, 1992, J Cell Sci. 103 (Pt 1):211-32)) and finally to lysosomes (pH 4.4 to 4.8), where acidic hydrolases lyse the internalized compounds, if these are biodegradable (Kornfeld et al., 1989, J Biol Chem 264(4):2212-20). Importantly, whether degraded or not, the materials internalized by endocytosis are confined within endo-lysosomal vesicles, which typically impedes their access to molecular targets located in the cytosol and other sub-cellular compartments.

In nature, some parasites, bacterial and viral pathogens that enter cells by classical endocytic mechanisms are able to gain access to intracellular compartments (e.g., the cytosol and, from there, the nucleus in certain cases) by escaping the endo-lysosomal vesicles in which they are contained (Cossart et al., 2004, Science 304(5668): 242-8; Campbell et al., 2005, Gene Ther. 12(18): 1353-9; Bonazzi et al., 2006, FEBS Lett 580(12):2962-7; Andrews et al., 1991, Parasitol Today 7(12):335-40). These pathogens have evolved mechanisms capable of "sensing" the decreasing pH within endosomes and lysosomes, e.g., by protonation of amphiphilic molecules which can permeate endo-lysosomal membranes.

The development of drug delivery systems that mimic the molecules and mechanism that render intracellular pathogens capable of crossing biological membranes has been pursued extensively. For instance, polycationic lipids, which are used to assist transfection of cells with DNA plasmids or small RNA molecules, bind negatively charged proteoglycans at the cell surface and thus favor cellular delivery. Disadvantageously, however, polycationic lipids form holes in the plasma membrane which causes cellular damage and death (Singh et al., 2004, Chem. Biol. 11(5):713-23; Dincer et al., 2005, Gene Ther. 12 Suppl 1:S139-45; Zuhorn et al., 2005, Mol. Ther. 11(5):801-10). In a related example, positively charged, arginine rich cell penetrating peptides (e.g., RGD and Tat) bind to the cell surface by electrostatic interactions and have been reported to facilitate subsequent intracellular delivery of conjugated cargoes (Melikov et al., 2005, Cell Mol Life Sci. 62(23):2739-49; Magzoub et al., 2005, Biochemistry 44(45): 14890-7; Suk et al., 2006, Biomaterials). However, it is remains uncertain whether these conjugates can cross the plasma membrane or are internalized within endo-lysosomal vesicles via natural endocytic pathways. Fusogenic peptides derived from bacterial toxins (e.g., hemagglutinin-derived, GALA peptides) are believed to induce formation of holes in the endosomal membrane upon internalization, due to changes in the peptide structure (e.g., from random coils to amphiphilic helixes capable of penetrate the endosomal membrane (Kakudo et al., 2004, Biochemistry 43(19):5618-28)), which occur in response to gradual pH lowering in these vesicular compartments. However, such fusogenic peptides, which have also been shown to permeate the plasma membrane (and therefore cause adverse effects including cell damage and death), appear to be effective only when presented to the cell as part of a phospholipid carriers, e.g., liposomes, which have formidable intrinsic limitations for delivery of many types of cargoes (e.g., proteins) and also have very limited circulation time in the bloodstream (Kakudo et al., 2004, Biochemistry 43(19):5618-28).

Other state-of-the-art means designed to overcome endosomal membranes without affecting the plasma membrane include polymer carriers that are sensitive to pH and temperature-responsive polyelectrolyte hydrogels (Yessine et al., 2004, Adv Drug Deliv Rev. 56(7):999-1021; Choi et al., 2006, Biomacromolecules 7(6): 1864-7015-26; Oishi et al., 2006, Bioconjug Chem. 17(3):677-88; Stayton et al., 2005, Orthod Craniofac Res. 8(3):2 19-25). Polymer carriers that can sense pH (e.g., acrylic acid derivatives) basically act as pH buffers and only become protonated when the endosomal pH decreases. However, currently available carriers with these characteristics render monomer non-biodegradable and are likely to be cytotoxic (Yessine et al., 2004, Adv Drug Deliv Rev. 56(7):999-1021; Oishi et al., 2006, Bioconjug Chem. 17(3):677-88; Stayton et al., 2005, Orthod Craniofac Res. 8(3):2 19-25). Permeating activity of temperature-responsive polyelectrolyte hydrogel carriers can be controlled after their internalization by varying the hydrogel hydration rate in a temperature dependent manner, which leads to changes in the carrier volume and results in lysis of the endo-lysosomal vesicle (Choi et al., 2006, Biomacromolecules 7(6): 1864-70). This procedure requires changes in temperature, which can be applied only to focal targets with well-known localization, hence disseminated targets and targets with unknown localization cannot be treated. This method is also highly invasive, which greatly restricts applications of this type of carriers. Finally, targeting of such types of nano-scale carriers in the vasculature remains to be designed and tested.

Thus, there is a need in the art for a method of delivering exogenous material into cells. The present invention addresses this need.

BRIEF SUMMARY OF THE INVENTION

The invention provides a composition comprising a DNA-based carrier and a targeting moiety. The invention also provides a pharmaceutical composition comprising a DNA-based carrier, a targeting moiety and a pharmaceutically-acceptable excipient. The DNA-based carrier may be selected from the group consisting of a DNA dendrimer, a double-stranded DNA, a single-stranded DNA, a single-stranded hairpin DNA and multimers thereof. Preferably, the DNA-based carrier is a DNA dendrimer. In some embodiments, the targeting moiety is linked to the DNA-based carrier.

The targeting moiety may bind to at least one of a cell surface protein, carbohydrate or lipid. In some embodiments, the targeting moiety binds to a cell adhesion molecule (CAM). The CAM may be selected from the group consist of intercellular adhesion molecule (ICAM), platelet-endothelial cell adhesion molecule (PECAM), activated leukocyte cell adhesion molecule (ALCAM), B-lymphocyte cell adhesion molecule (BL-CAM), vascular cell adhesion molecule (VCAM), mucosal vascular addressin cell adhesion molecule (MAdCAM), CD44, LFA-2, LFA-3, and basigin. In preferred embodiments, the CAM is ICAM or PECAM. On other embodiments, the targeting moiety binds to a cell surface molecule associated with classical endocytosis. Preferably, the cell surface molecule associated with classical endocytosis is one of mannose-6-phosphate receptor and transferrin receptor.

The targeting moiety may be selected from the group consisting of an antibody, an aptamer, a nucleic acid, a peptide, a carbohydrate, a lipid, a vitamin, a toxin, a component of a microorganism, a hormone, a receptor ligand and any derivative thereof. If the targeting moiety is an antibody, it may be selected from the group consisting of: a monoclonal antibody, a humanized antibody, a synthetic antibody, a heavy chain antibody, and a biologically active fragment of an antibody, wherein the biologically active fragment is a Fab fragment, a F(ab')$_2$ fragment, and a Fv fragment. In preferred embodiments, the targeting moiety is an antibody that binds to one of ICAM-1, PECAM-1, transferrin receptor and mannose-6-phosphage receptor.

In some embodiments, the composition further comprises a cargo selected from the group consisting of a biologically active agent, an imaging agent, a monitoring agent and combinations thereof. Optionally, the cargo is linked to the DNA-based carrier.

In some embodiments, the composition further comprises a secondary carrier selected from the group consisting of a liposome, a non-DNA dendrimer, a polymer carrier, a microbubble, a paramagnetic particle, a ferromagnetic particle, a self-assembled polymer, a polymersome, a filomicelle, an albumin particle, and a lipoprotein. In some embodiments, the targeting moiety is linked to the secondary carrier.

Also provided are methods of using the compositions of the invention to deliver a cargo to a cell. In one aspect, the method comprises the steps of contacting a cell with a DNA-based carrier and a cargo, wherein the DNA-based carrier comprises a targeting moiety, and wherein the targeting moiety binds the cell, thereby delivering the cargo to the cell. In another aspect, the method comprises contacting a mammalian cell with a DNA-based carrier and a cargo, wherein the DNA-based carrier comprises a targeting moiety, and wherein the targeting moiety binds to at least one of a cell surface protein, carbohydrate or lipid on the, thereby delivering the cargo to the mammalian cell. In preferred embodiments, the cargo is delivered to the cytosol of the cell. In some embodiments, the cell is selected from the group of an epithelial cell, an endothelial cell, a fibroblast cell and a mesothelial cell. In preferred embodiments, the cell is a human cell.

In some embodiments of the methods, the DNA-based carrier is selected from the group consisting of a DNA dendrimer, a double-stranded DNA, a single-stranded DNA, a single-stranded hairpin DNA and multimers thereof. Preferably, the DNA-based carrier is a DNA dendrimer. In some embodiments, the targeting moiety is linked to the DNA-based carrier.

In some embodiments of the methods, the targeting moiety may bind to at least one of a cell surface protein, carbohydrate or lipid. In some embodiments, the targeting moiety binds to a cell adhesion molecule (CAM). The CAM may be selected from the group consist of intercellular adhesion molecule (ICAM), platelet-endothelial cell adhesion molecule (PECAM), activated leukocyte cell adhesion molecule (ALCAM), B-lymphocyte cell adhesion molecule (BL-CAM), vascular cell adhesion molecule (VCAM), mucosal vascular addressin cell adhesion molecule (MAdCAM), CD44, LFA-2, LFA-3, and basigin. In preferred embodiments, the CAM is ICAM or PECAM. On other embodiments, the targeting moiety binds to a cell surface molecule associated with classical endocytosis. Preferably, the cell surface molecule associated with classical endocytosis is one of mannose-6-phosphate receptor and transferrin receptor.

In some embodiments of the methods, the targeting moiety is selected from the group consisting of an antibody, an aptamer, a nucleic acid, a peptide, a carbohydrate, a lipid, a vitamin, a toxin, a component of a microorganism, a hormone, a receptor ligand and any derivative thereof. If the targeting moiety is an antibody, it may be selected from the group consisting of: a monoclonal antibody, a humanized antibody, a synthetic antibody, a heavy chain antibody, and a biologically active fragment of an antibody, wherein the biologically active fragment is a Fab fragment, a F(ab')$_2$ fragment, and a Fv fragment. In preferred embodiments, the targeting moiety is an antibody that binds to one of ICAM-1, PECAM-1, transferrin receptor and mannose-6-phosphage receptor.

In some embodiments of the methods, the cargo selected from the group consisting of a biologically active agent, an imaging agent, a monitoring agent and combinations thereof. In some aspects, the biologically active agent is a therapeutic agent. Optionally, the cargo is linked to the DNA-based carrier.

In some embodiments of the methods, the cell is also contacted with a secondary carrier selected from the group consisting of a liposome, a non-DNA dendrimer, a polymer carrier, a microbubble, a paramagnetic particle, a ferromagnetic particle, a self-assembled polymer, a polymersome, a filomicelle, an albumin particle, and a lipoprotein. In some embodiments, the targeting moiety is linked to the secondary carrier.

In some embodiments of the method, the cell is contacted with a composition comprising a DNA-based carrier, a targeting moiety and a cargo. In other embodiments, the cell is contacted with the components separately or in any subcombination.

The invention also provides kits useful in practicing the methods of the invention. The kit comprises a DNA-based carrier and a targeting moiety and an instructional material. Optionally, the targeting moiety is linked to the DNA-based carrier. In some kits, the DNA-based carrier is selected from the group consisting of a DNA dendrimer, a double-stranded DNA, a single-stranded DNA, a single-stranded hairpin DNA and multimers thereof. In some kits, the kit further comprises a secondary carrier selected from the group consisting of a liposome, a non-DNA dendrimer, a polymer carrier, a microbubble, a paramagnetic particle, a ferromagnetic particle, a self-assembled polymer, a polymersome, a filomicelle, an albumin particle, and a lipoprotein. Optionally, the targeting moiety is linked to the secondary carrier. In some embodiments, the kit further comprises a cargo selected from the group consisting of a biologically active agent, an imaging agent, a monitoring agent and combinations thereof.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1A depicts anti-ICAM/Bds bound to plasma membrane (indicated by two arrows) and inside the intracellular vacuole (indicated by single arrow). FIG. 1B depicts numerous anti-ICAM/Bds localized intracellularly within electron dense, endo-lysosomal compartments (indicated by arrows).

FIG. 2A depicts a schematic of anti-mouse IgG-conjugated DNA dendrimers coupled to mouse anti-rat IgG and either rat anti-mouse ICAM-1 (top of schematic) or to rat IgG (bottom of schematic). FIG. 2B is a bar graph of the in vivo organ distribution of $^{125}$I-labeled dendrimers. The y-axis is the ratio of the percent of the injected dose per gram of organ (% ID/g) of anti-ICAM/Dend to the % ID/g of IgG/Dend. FIG. 2C depicts a schematic of anti-mouse IgG-conjugated DNA dendrimers coupled to fluorescent mouse anti-human ICAM-1 (top of schematic) or to fluorescent mouse IgG (bottom of schematic). FIG. 2D are representative fluorescent images of HUVEC cells cultured with fluorescent dendrimers as indicated. The inset is a phase-contrast micrograph image.

FIG. 3A is a pair of images of HUVEC (human umbilical vein endothelial cells) cells incubated with anti-ICAM/Dend at 4° C. or 37° C. for 1 hour. Texas red staining depicts surface-bound dendrimers. FITC staining depicts intracellularly-localized dendrimers. FIG. 3B is a pair of images of HUVEC cells incubated with anti-ICAM/Dend for 1 hour at 37° C. (lefthand images) or for 1 hour at 37° C. followed by washing of non-bound dendrimers and an additional 2 hours of incubation at 37° C. (righthand images). Insets show images of cells incubated with anti-ICAM-coupled polystyrene beads used as controls for vesicular localization of the internalized materials. FIG. 3C is a series of representative fluorescent images showing internalization within HUVEC cells of DNA dendrimers targeted to transferrin receptor (anti-TrfR/Dend) or mannose-6-phosphate receptor (anti-M6PR/Dend), both associated with classical mechanisms of endocytosis by clathrin-coated pits, or to PECAM-1 (anti-PECAM/Dend), associated with non-classical CAM-endocytosis. FIG. 3D is a series of representative fluorescent images showing internalization of anti-ICAM/Dend in human REN mesothelioma cancer cells and human skin fibroblasts. Insets in FIGS. 3C and 3D are representative images of the same cell types incubated with dendrimer formulations wherein the anti-mouse IgG recognizes the entirety of the mouse IgG targeting moiety, not just the Fc portion. The full-size images used a dendrimer formulation wherein the anti-mouse IgG recognized only the Fc portion of the mouse IgG targeting moiety, which is expected to enable a more advantageous orientation of the binding portion of the mouse IgG with respect to the dendrimer exterior.

FIGS. 4A and 4B are a series of representative fluorescence micrograph images of HUVEC cells incubated with a cargo material and either anti-ICAM/Bds or anti-ICAM/Dend. In FIG. 4A, the cargo material was Texas Red dextran to determine intracellular cytosolic delivery. In FIG. 4B, the cargo was ethidium homodimer-1 to detect nuclear delivery. Left-hand panels in each pair of images are phase-contrast images of cells in the samples. Right-hand panels identify localization of fluorescently-labeled ethidium in cells.

FIGS. 5A and 5B are a series of representative images of HUVEC cells incubated with a cargo material and either anti-ICAM/Bds or anti-ICAM/Dend. In FIG. 5A, the cargo was biotinylated phalloidin, whose binding to F-actin in the cytosol was detected by staining with Texas Red streptavidin. In FIG. 5B, the cargo was fluorescent albumin conjugated to a nuclear localization sequence to facilitate its transport to the nucleus. In FIGS. 4 and 5, cells incubated at 4° C. served as a control for plasma membrane integrity, and permeabilized cells served as a control for free access of the indicated cargoes to cytosol and intracellular compartments. Left-hand panels for each pair of images are phase-contrast images.

FIG. 6A is a bar graph depicting the percent protection against hydrogen peroxide ($H_2O_2$)-induced oxidative injury of cells under different conditions. Data are calculated as percent of protection against $H_2O_2$ induced injury, where cells incubated in the absence of $H_2O_2$ and catalase represent 100% protection (vehicle), and cells pre-treated with anti-ICAM/Bds+catalase represent no protection by 3 hours post-internalization of the beads. FIG. 6B depicts representative images of HUVEC cells incubated with media containing anti-ICAM/

Dend and a plasmid encoding Rac-EGFP protein. FIG. 6C depicts representative images of HUVEC cells incubated with media containing naked plasmid (top images) or with media containing anti-ICAM/Bds and plasmid. In FIGS. 6B and 6C, the lefthand image of each pair is a phase-contrast microscopy image. The righthand image is a fluorescence microscopy image.

FIG. 7A depicts the number of cells observed 48 hours after a 5 hour incubation in the presence or absence of anti-ICAM/Dend. FIG. 7B depicts the percent viability of the cells.

DETAILED DESCRIPTION OF THE INVENTION

Figure 1A:
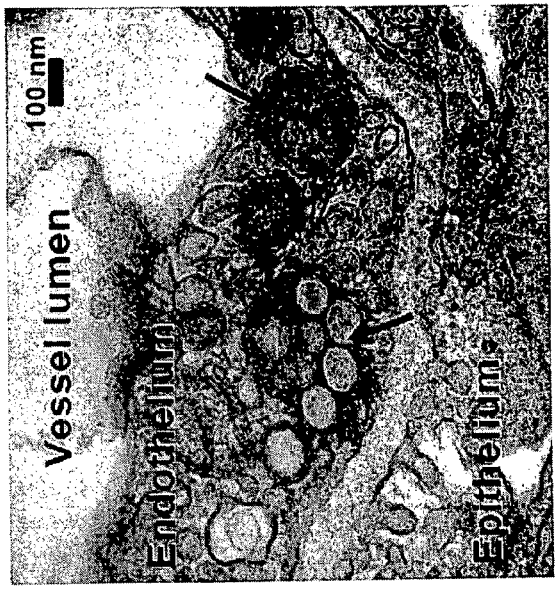
FIGS. 1A and 1B are a series of representative electron micrograph images of in vivo endocytosis by endothelial cells lining pulmonary vessels of anti-ICAM-targeted polystyrene beads (anti-ICAM/Bds; mean diameter 150 nm) injected intravenously into intact anesthetized mice.

The invention provides a method of delivering a cargo to a cell using DNA as a carrier. In preferred embodiments, the DNA-based carrier is a DNA dendrimer targeted to the cell by a targeting moiety. In preferred embodiments, the cargo is internalized by the cell by an endocytic mechanism. The method is a universal approach that enables delivery of exogenous materials to the cytosol and thereby to other intracellular compartments accessible from the cytosol. The method further encompasses delivering endogenous materials into the cytosol of a cell. The invention further provides compositions comprising a targeted DNA-based carrier and kits useful in the practice of the method.

DEFINITIONS

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization are those well known and commonly employed in the art.

The techniques and procedures for recombinant manipulations, including nucleic acid and peptide synthesis, are generally performed according to conventional methods in the art and various general references (e.g., Sambrook et al, 2001, Molecular Cloning, A Laboratory Approach, Cold Spring Harbor Laboratory Press, Cold Spring Harbor, N.Y.; Ausubel et al., eds, 2005, Current Protocols in Molecular Biology, John Wiley & Sons, New York, N.Y.; and Gerhardt et al., eds., 1994, Methods for General and Molecular Bacteriology, American Society for Microbiology, Washington, D.C.), which are provided throughout this document.

The nomenclature used herein and the laboratory procedures used in analytical chemistry and organic syntheses described below are those well known and commonly employed in the art. Standard techniques or modifications thereof, are used for chemical syntheses and chemical analyses.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

It is understood that any and all whole or partial integers between any ranges set forth herein are included herein.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. The antibodies useful in the present invention may exist in a variety of forms including, for example, polyclonal antibodies, monoclonal antibodies, intracellular antibodies ("intrabodies"), Fv, Fab and F(ab)$_2$, as well as single chain antibodies (scFv), camelid antibodies and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

As used herein, the term "heavy chain antibody" or "heavy chain antibodies" comprises immunoglobulin molecules derived from camelid species, either by immunization with an antigen and subsequent isolation of sera, or by the cloning and expression of nucleic acid sequences encoding such antibodies. The term "heavy chain antibody" or "heavy chain antibodies" further encompasses immunoglobulin molecules isolated from an animal with heavy chain disease, or prepared by the cloning and expression of $V_H$ (variable heavy chain immunoglobulin) genes from an animal.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

As used herein, "aptamer" refers to a small molecule that can bind specifically to another molecule. Aptamers are typically either polynucleotide- or peptide-based molecules. A polynucleotidal aptamer is a DNA or RNA molecule, usually comprising several strands of nucleic acids, that adopt highly specific three-dimensional conformation designed to have appropriate binding affinities and specificities towards specific target molecules, such as peptides, proteins, drugs, vitamins, among other organic and inorganic molecules. Such polynucleotidal aptamers can be selected from a vast population of random sequences through the use of systematic evolution of ligands by exponential enrichment. A peptide aptamer is typically a loop of about 10 to about 20 amino acids attached to a protein scaffold that bind to specific ligands. Peptide aptamers may be identified and isolated from combinatorial libraries, using methods such as the yeast two-hybrid system.

As used herein, "classical endocytic pathways" refers to the following types of endocytosis: (a) clathrin-mediated, (b) caveolar-mediated, (c) phagocytosis, and (d) macropinocytosis. Macropinocytosis is dynamin independent. The other three are dynamin dependent.

As used herein, "non-classical endocytic pathways" refers to any endocytic pathway that is not one of the four classical endocytic pathways. Exemplary non-classical pathways include: (a) cell adhesion molecule (CAM)-mediated endocytosis (dynamin dependent), and (b) other pathways known in the art and having no specific name, classified as dynamin dependent or dynamin independent mechanisms.

"Cell surface molecule" as used herein refers to a molecule that has at least a portion present at the surface of a cell, such as receptors and plasma membrane components. A cell surface molecule may or may not comprise a transmembrane portion. A cell surface molecule may or may not be associated with other molecules that are not cell surface molecules.

As used herein, a cell surface molecule is "associated with classical endocytosis" when binding by an agent to the cell surface molecule results in endocytic internalization of the bound agent by a classical endocytic pathway. For instance, the transferrin receptor is a cell surface molecule associated with classical endocytosis as binding by the receptor ligand or by an antibody against the receptor induces endocytosis.

As used herein, a cell surface molecule is "associated with non-classical endocytosis" when binding by an agent to the cell surface molecule results in endocytic internalization of the bound agent by a non-classical endocytic pathway. For instance, the ICAM-1 is a cell surface molecule associated with non-classical endocytosis as binding by antibody-coated carriers against the ICAM-1 induces CAM-mediated endocytosis.

"Complementary" as used herein refers to the broad concept of subunit sequence complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are substantially complementary to each other when at least about 50%, preferably at least about 60% and more preferably at least about 80% of corresponding positions in each of the molecules are occupied by nucleotides which normally base pair with each other (e.g., A:T and G:C nucleotide pairs).

As used herein, a "DNA-based carrier" refers to a drug delivery system that comprises nucleic acid. A non-limiting example of a DNA-based carrier is a DNA dendrimer. Other DNA-based carriers include double-stranded DNA, single-stranded DNA and single-stranded hairpin DNA, multimers thereof.

As used herein, a "DNA dendrimer" or "dendrimer" refers to a matrix of polynucleotides, exhibiting regular branching, formed by the sequential or generational addition of branched layers to or from a core molecule, such as an initiating monomer.

As used herein, an "initiating monomer" is a polynucleotide compound that serves to nucleate the formation of a dendrimer.

As used herein, an "extending monomer" is a polynucleotide compound that can bind to the initiating monomer and/or to each other during assembly of a dendrimer. Extending monomers form the layers of the dendrimer. The first layer of a dendrimer is the layer of extending monomers closest to the initiating monomer. The outer layer is the layer furthest from the initiating monomer and forming the surface of the dendrimer. Extending monomers are also referred to in the art as matrix monomers, matrix extending monomers and matrix polynucleotide monomers.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a symptom of the disease or disorder, the frequency with which such a symptom is experienced by a patient, or both, are reduced.

By the term "applicator," as the term is used herein, is meant any device including, but not limited to, a hypodermic syringe, a pipette, and the like, for administering the compounds and compositions of the invention.

The terms "effective amount" and "pharmaceutically effective amount" refer to a nontoxic but sufficient amount of an agent to provide the desired biological result. That result can be reduction and/or alleviation of the signs, symptoms, or causes of a disease or disorder, or any other desired alteration of a biological system. An appropriate effective amount in any individual case may be determined by one of ordinary skill in the art using routine experimentation.

"Antisense" refers particularly to the nucleic acid sequence of the non-coding strand of a double stranded DNA molecule encoding a protein, or to a sequence which is substantially homologous to the non-coding strand. As defined herein, an antisense sequence is complementary to the sequence of a double stranded DNA molecule encoding a protein. It is not necessary that the antisense sequence be complementary solely to the coding portion of the coding strand of the DNA molecule. The antisense sequence may be complementary to regulatory sequences specified on the coding strand of a DNA molecule encoding a protein, which regulatory sequences control expression of the coding sequences.

"Instructional material," as that term is used herein, includes a publication, a recording, a diagram, or any other medium of expression which can be used to communicate the usefulness of the composition and/or compound of the invention in a kit. The instructional material of the kit may, for example, be affixed to a container that contains the compound and/or composition of the invention or be shipped together with a container which contains the compound and/or composition. Alternatively, the instructional material may be shipped separately from the container with the intention that the recipient uses the instructional material and the compound cooperatively. Delivery of the instructional material may be, for example, by physical delivery of the publication or other medium of expression communicating the usefulness of the kit, or may alternatively be achieved by electronic transmission, for example by means of a computer, such as by electronic mail, or download from a website.

"Naturally-occurring" as applied to an object refers to the fact that the object can be found in nature. For example, a polypeptide or polynucleotide sequence that is present in an organism (including viruses) that can be isolated from a source in nature and which has not been intentionally modified by man is a naturally-occurring sequence.

As used herein, "endogenous" refers to a naturally-occurring molecule originating or produced within an organism, tissue, or cell. Endogenous also includes agents present in an organism not originating or produced by the organism but present by infection or environmental exposure. Such agents include, but are not limited to, toxins, viruses and bacteria.

As used herein, "exogenous" refers to a molecule which does not originate in an organism, tissue or cell. An endogenous material that is removed from an organism and is re-introduced in the method of the invention is considered an exogenous material.

In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

A "polynucleotide" means a single strand or parallel and anti-parallel strands of a nucleic acid. Thus, a polynucleotide may be either a single-stranded or a double-stranded nucleic acid.

The term "oligonucleotide" typically refers to short polynucleotides, generally no greater than about 60 nucleotides. It will be understood that when a nucleotide sequence is represented by a DNA sequence (i.e., A, T, G, C), this also includes an RNA sequence (i.e., A, U, G, C) in which "U" replaces "T."

By "nucleic acid" is meant any nucleic acid, whether composed of deoxyribonucleosides or ribonucleosides, and whether composed of phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages. The term nucleic acid also specifically includes nucleic acids composed of bases other than the five biologically occurring bases (adenine, guanine, thymine, cytosine and uracil). The term "nucleic acid" typically refers to large polynucleotides.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

By "expression cassette" is meant a nucleic acid molecule comprising a coding sequence operably linked to promoter/regulatory sequences necessary for transcription and, optionally, translation of the coding sequence.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a n inducible manner.

An "inducible" promoter is a nucleotide sequence which, when operably linked with a polynucleotide which encodes or specifies a gene product, causes the gene product to be produced substantially only when an inducer which corresponds to the promoter is present.

"Polypeptide" refers to a polymer composed of amino acid residues, related naturally occurring structural variants, and synthetic non-naturally occurring analogs thereof linked via peptide bonds. Synthetic polypeptides can be synthesized, for example, using an automated polypeptide synthesizer.

The term "protein" typically refers to large polypeptides. The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

As used herein, a "peptidomimetic" is a compound containing non-peptidic structural elements that is capable of mimicking the biological action of a parent peptide. A peptidomimetic may or may not comprise peptide bonds.

"Probe" refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions. Probes can be labeled with, e.g., chromogenic, radioactive, or fluorescent moieties and used as detectable moieties.

"Ribozymes" as used herein are RNA molecules possessing the ability to specifically cleave other single-stranded RNA in a manner analogous to DNA restriction endonucleases. Through the modification of nucleotide sequences encoding these RNAs, molecules can be engineered to recognize specific nucleotide sequences in an RNA molecule and cleave it (Cech, 1988, J. Amer. Med. Assn. 260:3030). There are two basic types of ribozymes, namely, tetrahymena-type (Hasselhoff, 1988, Nature 334:585) and hammerhead-type. Tetrahymena-type ribozymes recognize sequences which are four bases in length, while hammerhead-type ribozymes recognize base sequences 11-18 bases in length. The longer the sequence, the greater the likelihood that the sequence will occur exclusively in the target mRNA species. Consequently, hammerhead-type ribozymes are preferable to tetrahymena-type ribozymes for inactivating specific mRNA species, and 18-base recognition sequences are preferable to shorter recognition sequences which may occur randomly within various unrelated mRNA molecules. Ribozymes and their use for inhibiting gene expression are also well known in the art (see, e.g., Cech et al., 1992, J. Biol. Chem. 267:17479-17482; Hampel et al., 1989, Biochemistry 28:4929-4933; Eckstein et al., International Publication No. WO 92/07065; Altman et al., U.S. Pat. No. 5,168,053).

As used herein, "single stranded hairpin DNA" refers to a single strand of DNA having a sequence such that certain portions of the same strand have complementarity and can fold into a double strand conformation.

As used herein, a "targeting moiety" refers to a molecule that binds specifically to a molecule present on the cell surface of a target cell.

As used herein, a "targeted DNA-based carrier" and "a DNA-based carrier comprises a targeting moiety" refers to a composition comprising a DNA-based carrier and a targeting moiety. The targeting moiety may be linked directly, or by means of a linker, to the DNA-based carrier. Alternatively, the targeting moiety may be linked to another molecule, such as a cargo molecule or a secondary, non-nucleic acid carrier in the composition. The DNA-based carrier is targeted by virtue of being present in the same composition with the targeted cargo or targeted secondary carrier.

By the term "specifically binds," as used herein, is meant a molecule, such as an antibody, which recognizes and binds to a cell surface molecule or feature, but does not substantially recognize or bind other molecules or features in a sample.

As used herein, "conjugated" refers to covalent attachment of one molecule to a second molecule.

DESCRIPTION

The invention springs in part from the observation that DNA materials, such as DNA dendrimers, can be targeted to non-classical endocytic pathways, as well as classical endocytic pathways and facilitate the internalization and cytosolic delivery of a variety of cargoes, including small molecules, sugars, proteins and nucleic acids, to a wide variety of cell types without causing plasma membrane disruption or other harmful effects on cell viability. This observation is unexpected because DNA molecules, which have a net negative charge on their phosphate backbones at neutral pH, do not generally bind or cross plasma membrane, nor do they get internalized by endocytic mechanisms. Furthermore, DNA dendrimers, which are on the order of 130-150 nm in diameter, are not a priori expected to be compatible with endocytic vesicles formed during clathrin- or caveolar-mediated endocytosis, which are about 100 nm and about 70 nm in diameter, respectively (Muro et al., 2004, Curr Vasc Pharmacol. 2(3):281-99). DNA dendrimer size (in the nanometer ranges) is also not within the vesicle size, typically large, micron-sized objects, that induces macropinocytosis and phagocytosis.

As shown herein, DNA dendrimers targeted to receptors representative of cell surface molecules associated with classic endocytosis, are endocytosed and delivered efficiently into the cytosol. Specifically, DNA dendrimers targeted to either mannose-6-phosphate receptor (M6PR) or transferrin receptor (TrfR), which are associated with classical endocytosis (in particular, clathrin-mediated endocytosis), are efficiently endocytosed and delivered to the cytosol. Furthermore, DNA dendrimers targeted to molecules representative of molecules associated with non-classical endocytic pathways, are also endocytosed and delivered into the cytosol. Without wishing to be bound by theory, it is believed that ICAM-1 and PECAM-1 targeted DNA dendrimers are taken up by CAM-mediated endocytosis, an unusual type of endocytosis that does not involve clathrin, caveolae, macropinocytosis or phagocytosis. PECAM-1 and ICAM-1, an Ig-like transmembrane glycoprotein expressed at the luminal surface of endothelial cells (and other cell types in the case of ICAM-1), are involved in leukocyte adhesion to cells, but are not an endocytic receptor (Springer, 1994, Cell 76(2):301-14; Almenar-Queralt et al., 1995, Am J Pathol. 147(5): 1278-88; Diamond et al., 1991, Cell 65(6):961-71; Newman and Albelda, 1992, Nouv Rev Fr Hematol 32(Suppl):S9-13). Cells expressing PECAM-1 or ICAM-1 do not internalize anti-PECAM-1 antibodies or anti-ICAM-1 antibodies. Paradoxically, however, ICAM-1 or PECAM-1 clustering by multivalent antibody complexes induces internalization via CAM-mediated endocytosis (Murciano et al., 2003, Blood 101(10):3977-84; Muro et al., 2003, J Cell Sci 116(Pt 8): 1599-609).

The mechanism by which targeted DNA dendrimers results in cytosolic delivery of cargo, avoiding lysosomal degradation, is unknown. Without wishing to be bound by theory, one potential explanation is that when targeted to a cell surface molecule that permits endocytosis, dendrimeric DNA has access to endosomes. The DNA dendrimers and accompanying cargo reside in the mildly acidic endosomal compartment. For instance, in CAM-endocytosed DNA dendrimers, the endocytosed dendrimers are thought to reside in an endosomal compartment for a relatively prolonged time, apparently due to the uniquely slow endosomal trafficking of the internalized cargoes. Endosome acidification may result in protonation of phosphate groups in the DNA dendrimer, rendering the hydrophobic DNA dendrimer capable of non-damaging permeation of the endosomal membrane. However, the invention should be not be construed as limited by the mechanism by which the targeted DNA dendrimers are delivered to the cytosol without plasma membrane poration or otherwise impairing cell viability.

It has also been discovered that targeted DNA dendrimer delivery, for instance ICAM-1 targeted delivery, reduces or precludes lysosomal delivery and degradation. This result is also unexpected because in the prior art, targeted delivery systems were observed to undergo intracellular trafficking via endosomal vesicles to lysosomal delivery and degradation (in most cases) (Muro et al., 2003, Am J Physiol Cell Physiol. 285(5):C1339-47; Muro et al., 2006, Am J Physiol Lung Cell Mol. Physiol. 290(5):L809-17; Muro et al., 2005, Blood 105(2):650-8; Muro et al., 2006, Mol. Ther. 13(1): 135-41[Epub 2005 Sep. 8]). Avoiding or limiting lysosomal delivery and degradation by the method of the invention thus prolongs the duration of the effect of the cargo and thereby increases the effectiveness of the cargo delivered, compared to other delivery means. It is also contemplated that increasing the effectiveness of a cargo, for instance a therapeutic, will enable the reduction in the amount of cargo needed to achieve a given result. Consequently, the method of the invention may also reduce or minimize potential side effects of a cargo, such as a therapeutic. Also, cytosolic delivery is advantageous in permitting access to other cellular compartments, for instance, the nucleus. Furthermore, DNA-based carriers, such as DNA dendrimers, are biodegradable by endogenous DNAses within cells and therefore do not exert overt toxicity.

Thus, DNA-based carriers, such as DNA dendrimers, targeted to cell surface molecules (e.g., ICAM-1, PECAM-1, TrfR or M6PR) provide site-specific targeting and highly efficient and active internalization within cells and are therefore useful in methods of delivering molecules into cells. Such targeted DNA-based carriers do not passively cross the plasma membrane but are apparently internalized by endocytic pathways. Depending on the cell surface molecule serving as a target, the internalization pathway can be mediated by classical or non-classical mechanism. Classical pathways are ubiquitous and highly active in physiological conditions. Certain non-classical pathways, such as CAM-mediated endocytosis, are not restricted by size constraint of classical pathways, and are not affected under certain pathological conditions that suppress classical endocytic pathways. Most classical and non-classical endocytic pathways are characterized by passage of the internalized materials through intracellular pre-lysosomal vesicles. The method of the invention is useful in any application requiring the intracellular delivery of a cargo.

I. DNA-Based Carrier

The invention may be carried out using any DNA-based carrier known in the art. DNA-based carriers include, but are not limited to, DNA dendrimers, double-stranded linear DNA, single-stranded linear DNA, and single-stranded hairpin DNA, formulated either as monomolecular structures or including several units of the conformation crosslinked together (e.g., multimers). In some embodiments, the DNA-based carrier may comprise a coding sequence for a cargo (e.g, a therapeutic agent, monitoring agent or biosensor). In some embodiments, the DNA-based carrier may comprise a nucleic acid targeting moiety. In other embodiments, the DNA-based carrier does not encode any cargo. Thus, in these embodiments, the DNA-based carrier is a separate component from the cargo. Similarly, in embodiments where a nucleic acid targeting moiety is present, the nucleic acid targeting moiety may be a separate component from the DNA-based carrier.

In a preferred embodiment, the DNA-based carrier is a DNA dendrimer. DNA dendrimers are spheroid particles (diameter typically about 130 to about 150 nm, although they can be designed to be other sizes) of flexible branches formed by inter-hybridized DNA monomers. Each DNA monomer is composed of two polynucleotide strands that share a central region of complementary sequences where the two strands hybridze to each other, leaving 4 terminal single-stranded polynucleotide portions. These terminal sequences are complementary among themselves, hence, they can hybridize (in layers) to terminal sequences of other DNA monomers. Optionally, DNA dendrimers comprise covalently cross-linked strands of DNA. See, for instance, Nilsen et al., J. Theor. Biol. 187:273-284 (1997) and U.S. Pat. Nos. 5,175,270 and 6,274,723.

DNA dendrimers have been described in the literature for improved detection of nucleic acids and other molecules, due to improved signal amplification (Mora et al., 2006, Mol Cell Probes 20(2): 114-20; Borucki et al., 2005, J Clin Microbiol. 43(7):3255-9; Li et al., 2005, Nat. Biotechnol. 23(7):885-9; Li et al., 2004, Nat Mater 3(1):38-42; Lowe et al., 2004, Cytometry A 60(2): 135-44). However, DNA-based carriers, such as DNA dendrimers, have never been proposed or tested for delivering materials to living systems, either in cell culture or laboratory animals.

DNA dendrimers are commercially available, for instance, from Genisphere® (Hatfield, Pa.). In addition, the structural design and assembly of DNA dendrimers is generally known in the art. See, for instance, U.S. Pat. Nos. 5,175,270 and 6,274,723, incorporated herein by reference in their entireties. An initiating monomer constitutes the approximate center of a dendrimer, depending on the type of branching in the dendrimer. The three-dimensional assembly of extending monomers around the initiating monomer forms the interior volume of the dendrimer. The last, outer layer of extending monomers forms the surface of the dendrimer. Thus, the assembly of a dendrimer results in a three-dimensional shape, typically but not exclusively, a roughly spherical shape comprising layers of extending monomers. The outer layer comprises numerous binding sites.

More specifically, DNA dendrimers useful in the methods of the invention may be prepared by protocols having the following features. (i) The starting material is a double-stranded duplex of DNA with 5' and 3' single-stranded overhangs, or "binding arms," attached to the duplex trunk (e.g., four binding arms total), called the "initiating monomer," which is descriptive of its role in the assembly of a dendrimer. Each initiating monomer's 5' and 3' binding arms are annealed to complementary binding arms on "extending monomers" that have similar composition and morphology. (ii) A subset of the four binding arms on each extending monomer is complementary to the binding arms on the initiating monomer. The non-complementary binding arms of the extending monomers are inactive for annealing to the initiating monomer. Typically, four extending monomers can anneal to the initiating monomer to yield a single-layer, or one-layer, dendrimer in solution. (iii) To add another layer of extending monomers to dendrimers, one typically adds similar but distinguishable extending monomers, in which each monomer has a subset of its four binding arms that is complementary to binding arms on the dendrimer. Thus, a one-layer dendrimer can be converted to a two-layer dendrimer, and so on, stepwise, until a desired size of dendrimer is reached. Typically, dendrimers of three or four layers are used.

After assembly, a DNA dendrimer is optionally cross-linked to maintain and stabilize the structure of the dendrimer. Crosslinking hybridized regions between monomers (i.e., inter-monomer crosslinking) or between monomers and the nucleic acids that carry detectable labels, as well as between trunk portions (intra-monomer crosslinking), can stabilize the structure of the polynucleotide dendrimer. Similarly, any hybridized region of any DNA-based carrier may be crosslinked to stabilize the carrier. Individual units of carrier may also be crosslinked into a polymolecular carrier. Such crosslinking chemistries are well known in the art. See, e.g., Cimino et al., Annu. Rev. Biochem. 54:1151-1193 (1985); Shi et al., Biochemistry 25:5895-5902 (1986); and Cimino et al., Biochemistry 25:3013-3020 (1986). See also U.S. Pat. No. 4,196,281. Non-limiting examples of suitable crosslinking agents include: psoralens (including but not limited to 8-methoxypsoralen and angelicin), mitomycin C, daunomycin, ethidium diazide, cisplatin, transplatin, carboplatin, 8-methoxypsoralen, mechlorethamine, oxaliplatin, and carbodiimide compounds, among others.

The polynucleotide strands used in the monomers of dendrimers or in the other DNA-based carriers, can be made using standard techniques for synthesis of nucleic acids. These techniques can be biological or chemical. The techniques and procedures are generally performed according to conventional methods in the art and in various general references (e.g., Sambrook et al., 2001, supra; Ausubel et al., eds., 2005, supra, and Gerhardt et al., eds., 1994, Methods for General and Molecular Bacteriology, American Society for Microbiology, Washington, D.C.).

In one embodiment, polynucleotides are chemically synthesized using methods known in the art. See, e.g., Gait, 1985, Oligonucleotide Synthesis: A Practical Approach (IRL Press, Oxford, England. In another embodiment, polynucleotides are synthesized enzymatically using the polymerase chain reaction (PCR). One PCR method suitable for generating single-stranded polynucleotides is multi-cycle PCR using a single primer, which thereby amplifies a single strand. Nucleic acids may be purified by any suitable means, as are well known in the art, prior to their use. For example, the nucleic acids can be purified by reverse phase or ion exchange HPLC, size exclusion chromatography or gel electrophoresis. The skilled artisan will recognize that the method of purification will depend in part on the size of the nucleic acid to be purified.

The outer layer of a DNA dendrimer typically has at least two types of binding arms. These binding arms are available for attaching one or more types of moieties. In the method of the invention, at least one moiety is a targeting moiety. Optionally, other moieties may be attached to these binding arms. Other moieties include a cargo molecule and a detectable chemical moiety, such as a photon-emitting molecule, e.g. a fluorophore.

In some embodiments, the DNA-based carrier is associated with a secondary carrier, which may serve as a scaffold for the DNA-based carriers. Examples of such secondary carriers include, but are not limited to, liposomes, non-DNA dendrimers, polymer carriers, microbubbles, paramagnetic and ferromagnetic particles, self-assembled polymers, polymersomes, filomicelles, albumin particles, lipoproteins, and the like. A self-assembled polymer is one that is formed by self assembly of monomolecular building blocks. These building blocks are typically amphiphilic copolymers, which comprise a hydrophilic component (such as, but not limited to, polyethylenimine or polyethyleneglycol) and a hydrophobic component (such a, but not limited to, aliphatic polyesters) into a core-shell-type structure. These structures that are not maintained by direct conjugation or crosslink of the building blocks are known to as micelles and can vary in their morphology, for instance from spherical micelles ("polymersomes") to elongated or filamentous rods ("filomicelles"). The sizes of these structures may also vary from the nanometer to the micrometer size range. Once formed by self assembly, these structures may alternatively be further crosslinked chemically to increase their stability. Hydrophobic cargoes can be embedded into the hydrophobic regions of the carrier, while hydrophilic cargoes can be incorporated into an internal aqueous core or to the external hydrophilic corona.

In some embodiments, the DNA-based carrier is linked to the surface of the secondary carrier. In other embodiments, the DNA-based carrier is not linked but is associated with the secondary carrier by virtue of being in the same composition. In all instances, the cargoes and targeting moieties can be linked to the DNA-based carrier, or to the scaffold carrier, using methods described herein and known in the art.

II. Targeting Moiety and Cell Surface Molecules

The DNA-based carrier is directed to a specific cell by linking a targeting moiety to the carrier, to a secondary carrier and/or a cargo. In one preferred embodiment, the target moiety is linked to the DNA-based carrier. In another preferred embodiment, the target moiety is linked to a secondary carrier. A targeting moiety may be an antibody, a naturally-occurring ligand for the receptor or a functional derivative thereof, a vitamin, a hormone, a small molecule mimetic of a naturally-occurring ligand, a peptide, a polypeptide, a peptidomimetic, a carbohydrate, a lipid, an aptamer, a nucleic acid, a toxin, a component of a microorganism, or any other molecule provided it binds specifically to the cell surface molecule and induces endocytosis of the bound moiety.

The targeting moiety binds specifically to a molecule on the cell surface of a target cell. Any cell surface molecule may be targeted provided binding of the targeted DNA-based carrier induces endocytosis. Non-limiting examples of cell surface molecule that may be targeted in the practice of the invention include cell surface proteins, carbohydrates and lipids. Cell surface molecules that may be targeted include molecules associated with classical endocytosis and those associated with non-classical endocytosis.

Classical endocytosis pathways include (a) clathrin-mediated, (b) caveolar-mediated, and (c) phagocytosis (all three are dynamin dependent), and (d) macropinocytosis (dynamin independent). In the following, the parenthetical terms are the ligands, vitamins, hormones, and/or agonists associated with the given cell surface molecule. Clathrin-mediated pathways include, but are not limited to, transferrin receptor (transferrin); mannose and mannose-6-phosphate receptors, which are glycoproteins, including enzymes, which present mannose and/or mannose-6-phosphate residues; e.g., α-N-acetylgalactosaminidase, acid lipase, α-galactosidase, glucocerebrosidase, α-L-iduronidase, iduronate sulfatase, α-mannosidase, α-L-fucosidase, sialidase, or acid sphingomyelinase, and other enzymes related to diseases such as Pompe Disease, GM1 gangliosidosis, Tay-Sachs disease, GM2 gangliosidosis, Sandhoff disease, Fabry disease, Gaucher disease, metachromatic leukodystrophy, Krabbe disease, Niemann-Pick disease type A, Niemann-Pick disease type B, Niemann-Pick disease type C, Niemann-Pick disease type D, Farber disease, Wolman disease, Hurler Syndrome, Scheie Syndrome, Hurler-Scheie Syndrome, Hunter Syndrome, Sanfilippo A Syndrome, Sanfilippo B Syndrome, Sanfilippo C Syndrome, Sanfilippo D Syndrome, Morquio A disease, Morquio B disease, Maroteaux-Lamy disease, Sly Syndrome, α-mannosidosis, β-mannosidosis, fucosidosis, aspartylglucosaminuria, sialidosis, mucolipidosis II, mucolipidosis III, mucolipidosis IV, Goldberg Syndrome, Schindler disease, cystinosis, Salla disease, infantile sialic acid storage disease, Batten disease, or infantile neuronal ceroid lipofuscinosis; P-selectin (CD24, P-selectin glycoprotein ligand or PSGL-1); E-selectin (PSGL, E-selectin ligand or ESL-1); VCAM-1 (alpha 4-beta 1 integrin or such as VLA-1); beta 2 adrenergic receptors (epinephrine and agonists such as procaterol, alprenol, salmefamol, formoterol, isoproterenol, etc); muscarinic and other acetylcholine receptors (acethylcholine, carbamylcholine, muscarine, nicotine, varenicline); D2 dopamine receptor (dopamine, raclopride, 7-hydroxydiprorpylaminotetralin, morphine, apomorphine, bromocriptine; vitronectin receptor (vitronectin); LDL and LDL family receptors (apoB in LDL and other apolipoproteins, apoE, receptor associated protein RAP); CXCR4 chemokine receptor (Stromal Cell-Derived Factor 1); T-cell receptor (a major histocompatibility complex molecule and a peptide); IgE receptor (IgE); vitellogenin receptor (vitellogenin); oxytocin receptor (oxytocin); angiotensin converting enzyme; thrombomodulin (thrombin, platelet factor 4) and others.

Caveolar-mediated pathways and related plasma membrane components include, but are not limited to: GPI-anchored proteins such as alkaline phosphatase (phosphoethanolamine, pyridoxal phosphate); urokinase plasminogen activator receptor (urokinase); hyaluronan-mediated motility receptor RHAMM (hyalunonan); thrombomodulin (thrombin, platelet factor 4); plasmalemma vesicle protein 1 or PV1; glycolipids such as GM1 ganglioside, mono-, di-, and tri-aloasialogangliosides; high affinity folate receptor (folate); insulin receptor (insulin); M1 muscarinic receptor; VEGF receptors (VEGF); connexins; glycoprotein gp90; glycoprotein gp60 (albumin); aminopeptidases, such as aminopeptidase P and aminopeptidase N; and others.

Phagocytosis pathways include, but are not limited to: C3 receptors (C3b portion of IgG); Fc gamma receptors (Fc portion of IgG); toll-like receptors or TLRs (CpG oligodeoxynucleotide, R-848, polyinosinic-polycytidylic acid), lectin-like oxidized LDL receptor LOX-1 (oxidized LDL) and others.

Macropinocytosis pathways are receptor-independent pathways that can be stimulated by interaction of epithelial growth factor to epithelial growth factor receptor; phosphatidylserine to phosphatidylserine receptor; TAT peptides to negatively charged regions of the plasma membrane; and others.

Non-classical endocytic pathways include (a) cell adhesion molecule-(CAM)-mediated endocytosis (dynamin dependent), and (b) other known pathways with no specific name, classified as dynamin dependent or dynamin independent mechanisms. Exemplary CAM-mediated endocytic pathways include CAM-mediated endocytosis: intercellular adhesion molecule 1 or ICAM-1; and platelet-endothelial cell adhesion molecule 1 or PECAM-1. To date, only anti-ICAM-1 complexes and anti-PECAM-1 complexes have induced CAM-mediated endocytosis, however, pseudoligands for each are known and are contemplated to induce the same endocytic process. Pseudoligands of ICAM-1 include alpha L-beta 2 integrin LFA-1, alpha M-beta 2 integrin Mac-1, major rhinovirus class, and fibrinogen and fibrin. Pseudoligands of PECAM-1 include PECAM-1 in neighboring cells and alpha v-beta 3 integrins.

Other non-classical pathways of endocytosis include: in some instances, placental major histocompatibility class MHC-related Fc receptor for IgG or FcRn; GPI-anchored proteins; ganglioside GM1 (to which cholera toxin B binds); unknown receptors utilized by simian virus 40 and ricin; the proteoglycan syndecan-4 (a receptor to fibroblast growth factors); MHC-related FcR for IgG; FcRn; interleukin 2 or IL-2 receptor (IL-2); glutamate receptor mGluR5, gamma c (γ$_c$) cytokine receptor, TGF-β receptor and the like.

Preferably, the targeted cell surface molecule associated with classical endocytosis is a molecule associated with clathrin-mediated endocytosis. In an embodiment, the molecule associated with clathrin-mediated endocytosis is selected from transferrin receptor and mannose-6-phosphate receptor. These receptors are broadly distributed in the body and are useful for targeting delivery across the blood-brain barrier, targeting angiogenic vessels in tumor vasculature (TrfR) and immune system cells (M6PR).

In another preferred embodiment, the target cell surface molecule is a cell adhesion molecule (CAM). Cell adhesion molecules useful in the invention include, but are not limited to, neural specific adhesion molecules (e.g., NCAM) and systemic intercellular adhesion molecules. Systemic CAMs include intercellular adhesion molecules (e.g., ICAM-1, ICAM-2, ICAM-3), platelet-endothelial cell adhesion molecule (PECAM), activated leukocyte cell adhesion molecule (ALCAM), B-lymphocyte cell adhesion molecule (BL-CAM), vascular cell adhesion molecule (VCAM), mucosal vascular addressin cell adhesion molecule (MAdCAM), CD44, LFA-2 (CD2), LFA-3 (CD58), basigin (CD147) and the like.

In a preferred embodiment, the targeting moiety is an antibody that specifically binds to a target cell surface molecule. In a particularly preferred embodiment, the targeting moiety is an antibody that binds to one of ICAM-1, PECAM-1, TrfR and M6PR. The antibody is selected from the group consisting of a polyclonal antibody, a monoclonal antibody, a humanized antibody, a synthetic antibody, a heavy chain antibody, and a biologically active fragment of an antibody, wherein the biologically active fragment is a Fab fragment, a F(ab')$_2$ fragment, an sc-Fv fragment.

When the antibody used as a targeting moiety in the compositions and methods of the invention is a polyclonal antibody (IgG), the antibody is generated by inoculating a suitable animal with the targeted cell surface molecule. Antibodies produced in the inoculated animal which specifically bind to the cell surface molecule are then isolated from fluid obtained from the animal. Antibodies may be generated in this manner in several non-human mammals such as, but not limited to goat, sheep, horse, camel, rabbit, and donkey. Methods for generating polyclonal antibodies are well known in the art and are described, for example in Harlow, et al. (1988, In: Antibodies, A Laboratory Manual, Cold Spring Harbor, N.Y.).

Monoclonal antibodies directed against a full length targeted cell surface molecule or fragments thereof may be prepared using any well known monoclonal antibody preparation procedures, such as those described, for example, in Harlow et al. (1988, In: Antibodies, A Laboratory Manual, Cold Spring Harbor, N.Y.) and in Tuszynski et al. (1988, Blood, 72:109-115). Human monoclonal antibodies may be prepared by the method described in U.S. patent publication 2003/0224490. Monoclonal antibodies directed against an antigen are generated from mice immunized with the antigen using standard procedures as referenced herein. Nucleic acid encoding the monoclonal antibody obtained using the procedures described herein may be cloned and sequenced using technology which is available in the art, and is described, for example, in Wright et al. (1992, Critical Rev. in Immunol. 12(3,4):125-168) and the references cited therein.

When the antibody used in the methods of the invention is a biologically active antibody fragment or a synthetic antibody corresponding to antibody to a targeted cell surface molecule, the antibody is prepared as follows: a nucleic acid encoding the desired antibody or fragment thereof is cloned into a suitable vector. The vector is transfected into cells suitable for the generation of large quantities of the antibody or fragment thereof. DNA encoding the desired antibody is then expressed in the cell thereby producing the antibody. The nucleic acid encoding the desired peptide may be cloned and sequenced using technology which is available in the art, and described, for example, in Wright et al. (1992, Critical Rev. in Immunol. 12(3,4):125-168) and the references cited therein. Alternatively, quantities of the desired antibody or fragment thereof may also be synthesized using chemical synthesis technology. If the amino acid sequence of the antibody is known, the desired antibody can be chemically synthesized using methods known in the art as described elsewhere herein.

The present invention also includes the use of humanized antibodies specifically reactive with targeted cell surface molecule epitopes. These antibodies are capable of binding to the targeted cell surface molecule. The humanized antibodies useful in the invention have a human framework and have one or more complementarity determining regions (CDRs) from an antibody, typically a mouse antibody, specifically reactive with a targeted cell surface molecule.

When the antibody used in the invention is humanized, the antibody can be generated as described in Queen, et al. (U.S. Pat. No. 6,180,370), Wright et al., (supra) and in the references cited therein, or in Gu et al. (1997, Thrombosis and Hematocyst 77(4):755-759), or using other methods of generating a humanized antibody known in the art. The method disclosed in Queen et al. is directed in part toward designing humanized immunoglobulins that are produced by expressing recombinant DNA segments encoding the heavy and light chain complementarity determining regions (CDRs) from a donor immunoglobulin capable of binding to a desired antigen, attached to DNA segments encoding acceptor human framework regions. Generally speaking, the invention in the Queen patent has applicability toward the design of substantially any humanized immunoglobulin. Queen explains that the DNA segments will typically include an expression control DNA sequence operably linked to the humanized immunoglobulin coding sequences, including naturally-associated or heterologous promoter regions. The expression control sequences can be eukaryotic promoter systems in vectors capable of transforming or transfecting eukaryotic host cells or the expression control sequences can be prokaryotic promoter systems in vectors capable of transforming or transfecting prokaryotic host cells. Once the vector has been incorporated into the appropriate host, the host is maintained under conditions suitable for high level expression of the introduced nucleotide sequences and as desired the collection and purification of the humanized light chains, heavy chains, light/heavy chain dimers or intact antibodies, binding fragments or other immunoglobulin forms may follow (Beychok, Cells of Immunoglobulin Synthesis, Academic Press, New York, (1979), which is incorporated herein by reference).

Human constant region (CDR) DNA sequences from a variety of human cells can be isolated in accordance with well known procedures. Preferably, the human constant region DNA sequences are isolated from immortalized B-cells as described in WO 87/02671. CDRs useful in producing the antibodies of the present invention may be similarly derived from DNA encoding monoclonal antibodies capable of binding to the targeted cell surface molecule. Such humanized antibodies may be generated using well known methods in any convenient mammalian source capable of producing antibodies, including, but not limited to, mice, rats, camels, llamas, rabbits, or other vertebrates. Suitable cells for constant region and framework DNA sequences and host cells in which the antibodies are expressed and secreted, can be obtained from a number of sources, such as the American Type Culture Collection, Manassas, Va.

One of skill in the art will further appreciate that the present invention encompasses the use of antibodies derived from camelid species. That is, the present invention includes, but is not limited to, the use of antibodies derived from species of the camelid family. As is well known in the art, camelid antibodies differ from those of most other mammals in that they lack a light chain, and thus comprise only heavy chains with complete and diverse antigen binding capabilities (Hamers-Casterman et al., 1993, Nature, 363:446-448). Such heavy-chain antibodies are useful in that they are smaller than conventional mammalian antibodies, they are more soluble than conventional antibodies, and further demonstrate an increased stability compared to some other antibodies. Camelid species include, but are not limited to Old World camelids, such as two-humped camels (*C. bactrianus*) and one humped camels (*C. dromedarius*). The camelid family further comprises New World camelids including, but not limited to llamas, alpacas, vicuna and guanaco. The production of polyclonal sera from camelid species is substantively similar to the production of polyclonal sera from other animals such as sheep, donkeys, goats, horses, mice, chickens, rats, and the like. The skilled artisan, when equipped with the present disclosure and the methods detailed herein, can prepare high-titers of antibodies from a camelid species. As an example, the production of antibodies in mammals is detailed in such references as Harlow et al., (1988, Antibodies: A Laboratory Manual, Cold Spring Harbor, N.Y.).

$V_H$ proteins isolated from other sources, such as animals with heavy chain disease (Seligmann et al., 1979, Immunological Rev. 48:145-167, incorporated herein by reference in its entirety), are also useful in the compositions and methods of the invention. The present invention further comprises variable heavy chain immunoglobulins produced from mice and other mammals, as detailed in Ward et al. (1989, Nature 341:544-546, incorporated herein by reference in its entirety). Briefly, $V_H$ genes are isolated from mouse splenic preparations and expressed in *E. coli*. The present invention encompasses the use of such heavy chain immunoglobulins in the compositions and methods detailed herein.

Antibodies useful as targeting moieties in the invention may also be obtained from phage antibody libraries. To generate a phage antibody library, a cDNA library is first obtained from mRNA which is isolated from cells, e.g., the hybridoma, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al. (2001, Molecular Cloning: A Laboratory Manual, Cold Spring Harbor Laboratory Press, Cold Spring Harbor, N.Y.).

Bacteriophage which encode the desired antibody, may be engineered such that the protein is displayed on the surface thereof in such a manner that it is available for binding to its corresponding binding protein, e.g., the antigen against which the antibody is directed. Thus, when bacteriophage which express a specific antibody are incubated in the presence of a cell which expresses the corresponding antigen, the bacteriophage will bind to the cell. Bacteriophage which do not express the antibody will not bind to the cell. Such panning techniques are well known in the art and are described for example, in Wright et al., (supra).

Processes such as those described above, have been developed for the production of human antibodies using M13 bacteriophage display (Burton et al., 1994, Adv. Immunol. 57:191-280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule. However, the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al., 1991, J. Mol. Biol. 222:581-597. Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1:837-839; de Kruif et al., 1995, J. Mol. Biol. 248:97-105).

Once expressed, whole antibodies, dimers derived therefrom, individual light and heavy chains, or other forms of antibodies can be purified according to standard procedures known in the art. Such procedures include, but are not limited to, ammonium sulfate precipitation, the use of affinity columns, routine column chromatography, gel electrophoresis, and the like (see, generally, R. Scopes, "Protein Purification", Springer-Verlag, N.Y. (1982)). Substantially pure antibodies of at least about 90% to 95% homogeneity are preferred, and antibodies having 98% to 99% or more homogeneity most preferred for pharmaceutical uses. Once purified, the antibodies may then be used to prepare a targeted DNA dendrimer.

Other types of targeting moieties useful in the invention may be obtained using standard methods known to the skilled artisan. Such methods include chemical organic synthesis or biological means. Biological means include purification from a biological source, recombinant synthesis and in vitro translation systems, using methods well known in the art.

A peptide may be chemically synthesized by Merrifield-type solid phase peptide synthesis. This method may be routinely performed to yield peptides up to about 60-70 residues in length, and may, in some cases, be utilized to make peptides up to about 100 amino acids long. Larger peptides may also be generated synthetically via fragment condensation or native chemical ligation (Dawson et al., 2000, Ann. Rev. Biochem. 69:923-960). An advantage to the utilization of a synthetic peptide route is the ability to produce large amounts of peptides, even those that rarely occur naturally, with relatively high purities, i.e., purities sufficient for research, diagnostic or therapeutic purposes.

Solid phase peptide synthesis is described by Stewart et al. in Solid Phase Peptide Synthesis, 2nd Edition, 1984, Pierce Chemical Company, Rockford, Ill.; and Bodanszky and Bodanszky in The Practice of Peptide Synthesis, 1984, Springer-Verlag, New York. At the outset, a suitably protected amino acid residue is attached through its carboxyl group to a derivatized, insoluble polymeric support, such as cross-linked polystyrene or polyamide resin. "Suitably protected" refers to the presence of protecting groups on both the α-amino group of the amino acid, and on any side chain functional groups. Side chain protecting groups are generally stable to the solvents, reagents and reaction conditions used throughout the synthesis, and are removable under conditions which will not affect the final peptide product. Stepwise synthesis of the oligopeptide is carried out by the removal of the N-protecting group from the initial amino acid, and coupling thereto of the carboxyl end of the next amino acid in the sequence of the desired peptide. This amino acid is also suitably protected. The carboxyl of the incoming amino acid can be activated to react with the N-terminus of the support-bound amino acid by formation into a reactive group, such as formation into a carbodiimide, a symmetric acid anhydride, or an "active ester" group, such as hydroxybenzotriazole or pentafluorophenyl esters.

Examples of solid phase peptide synthesis methods include the BOC method, which utilizes tert-butyloxycarbonyl as the α-amino protecting group, and the FMOC method, which utilizes 9-fluorenylmethyloxcarbonyl to protect the α-amino of the amino acid residues. Both methods are well-known by those of skill in the art.

Incorporation of N- and/or C-blocking groups may also be achieved using protocols conventional to solid phase peptide synthesis methods. For incorporation of C-terminal blocking groups, for example, synthesis of the desired peptide is typically performed using, as solid phase, a supporting resin that has been chemically modified so that cleavage from the resin results in a peptide having the desired C-terminal blocking group. To provide peptides in which the C-terminus bears a primary amino blocking group, for instance, synthesis is performed using a p-methylbenzhydrylamine (MBHA) resin, so that, when peptide synthesis is completed, treatment with hydrofluoric acid releases the desired C-terminally amidated peptide. Similarly, incorporation of an N-methylamine blocking group at the C-terminus is achieved using N-methylaminoethyl-derivatized DVB (divinylbenzene), resin, which upon hydrofluoric acid (HF) treatment releases a peptide bearing an N-methylamidated C-terminus. Blockage of the C-terminus by esterification can also be achieved using conventional procedures. This entails use of resin/blocking group combination that permits release of side-chain peptide from the resin, to allow for subsequent reaction with the desired alcohol, to form the ester function. FMOC protecting group, in combination with DVB resin derivatized with methoxyalkoxybenzyl alcohol or equivalent linker, can be used for this purpose, with cleavage from the support being effected by trifluoroacetic acid (TFA) in dicholoromethane. Esterification of the suitably activated carboxyl function, e.g. with dicyclohexylcarbodiimide (DCC), can then proceed by addition of the desired alcohol, followed by de-protection and isolation of the esterified peptide product.

Incorporation of N-terminal blocking groups may be achieved while the synthesized peptide is still attached to the resin, for instance by treatment with a suitable anhydride and nitrile. To incorporate an acetyl blocking group at the N-terminus, for instance, the resin-coupled peptide can be treated with 20% acetic anhydride in acetonitrile. The N-blocked peptide product may then be cleaved from the resin, de-protected and subsequently isolated.

Prior to its use as a targeting moiety for a DNA-based carrier in accordance with the invention, a peptide is purified to remove contaminants. In this regard, it will be appreciated that the peptide will be purified so as to meet the standards set out by the appropriate regulatory agencies. Any one of a number of a conventional purification procedures may be used to attain the required level of purity including, for example, reversed-phase high-pressure liquid chromatography (HPLC) using an alkylated silica column such as $C_4$-, $C_8$- or $C_{18}$-silica. A gradient mobile phase of increasing organic content is generally used to achieve purification, for example, acetonitrile in an aqueous buffer, usually containing a small amount of trifluoroacetic acid. Ion-exchange chromatography can be also used to separate polypeptides based on their charge. Affinity chromatography is also useful in purification procedures.

Antibodies and other peptide targeting moieties may be modified using ordinary molecular biological techniques to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The polypeptides useful in the invention may further be conjugated to non-amino acid moieties that are useful in their application. In particular, moieties that improve the stability, biological half-life, water solubility, and immunologic characteristics of the peptide are useful. A non-limiting example of such a moiety is polyethylene glycol (PEG).

To prepare a targeted DNA-based carrier, such as a DNA dendrimer, the targeting moiety is linked to the DNA-based carrier, or a secondary carrier or a cargo in the composition comprising the DNA-based carrier. A single targeting moiety may be linked to the DNA-based carrier or secondary carrier. Alternatively, a plurality of (e.g., two or more) targeting moieties are linked to the DNA-based carrier, secondary carrier or cargo. When a plurality of targeting moieties are linked to a carrier or cargo, the moieties may target the same cell surface molecule or may target different cell surface molecules. If targeting different cell surface molecules, these molecules may be associated with the same endocytic pathway or different endocytic pathways. If targeting different cell surface molecules, the cell surface molecules may be present on the same cell type or may be present on different cell types.

Linking may be non-covalent or covalent. A targeting moiety may be linked directly to one or more of the polynucleotide strands comprising the DNA-based carrier. Alternatively, a targeting moiety is linked to a linker molecule which is in turn linked to the DNA-based carrier. In a preferred embodiment, wherein the DNA-based carrier is a DNA dendrimer, the linker molecule is an oligonucleotide comprising a sequence substantially complementary to a sequence present in one of the binding arms on the surface of the DNA dendrimer. Thus, the targeting moiety is linked indirectly and noncovalently to the DNA dendrimer by hybridization of the oligonucleotide to a binding arm. This approach is also applicable to other DNA-based carriers. Optionally, the hybridized oligonucleotide is also cross-linked to the DNA dendrimer. Cross-linking chemistries are disclosed elsewhere herein. When not cross-linked, hybridization between the DNA dendrimer and an oligonucleotide linked to a targeting moiety should be sufficiently long-lived under the conditions of use. Determination of binding free energies for nucleic acid molecules is well known in the art (see, e.g., Turner et al., 1987, CSH Symp. Quant. Biol. LII pp. 123-133; Freier et al., 1986, Proc. Nat. Acad. Sci. USA 83:9373-9377; Turner et al., 1987, J. Am. Chem. Soc. 109:3783-3785; Chavali et al., 2005, Bioinformatics 21(20): 3918-3925).

In another embodiment, the linker is a secondary IgG Fc-specific antibody which is linked to the DNA-based carrier. In one aspect, the antibody specifically binds to the Fc portion of the primary IgG antibody, e.g., the targeting moiety (see FIG. 2C) or an intervening antibody (see FIG. 2A). The secondary antibody is preferably specific for the species source of the primary antibody. For instance, if the targeting moiety is a human IgG antibody, the secondary antibody is anti-human IgG. In another aspect, the secondary antibody recognizes epitopes of the entire primary antibody, not just the Fc portion. Alternatively, the linker is an Fc gamma receptor that binds specifically to the Fc portion of an IgG antibody. In any of these, the carrier may be readily linked to any targeting moiety that is an IgG antibody.

Non-covalent linkages useful in the present invention include affinity binding pairs, such as biotin-streptavidin and immunoaffinity, having sufficiently high affinity to maintain the linkage during use and are well-known in the art. The art is also replete with conjugation chemistries useful for covalently linking a target moiety to a DNA-based carrier, secondary carrier or cargo, directly or via a linker. Art-recognized covalent coupling techniques are disclosed, for instance, in U.S. Pat. Nos. 5,416,016, 6,335,435, 6,528,631, 6,861,514 and 6,919,439, incorporated herein by reference in their entirety. Other conjugation chemistries are disclosed in U.S. Patent Publication No. 20040249178, incorporated herein by reference in its entirety. Still other conjugation chemistries include: p-hydroxy-benzoic acid linkers (Chang-Po et al., 2002, Bioconjugate Chem. 13(3):525-529); native ligation (Stetsenko et al., 2000, J Org. Chem. 65:4900-4908): disulfide bridge conjugates (Oehlke et al., 2002, Eur J. Biochem. 269:4025-4032 and Rogers et al., 2004, Nuc Acids Res. 32(22) 6595-6604); maleimide linkers (Zhu et al., 1993, Antisense Res Dev. 3:265-275); thioester linkers (Ede et al., 1994, Bioconjug Chem. 5:373-378); Diels-Alder cycloaddition (Marchán et al., 2006. Nuc Acids Res. 34(3): e24, 2006 Feb. 14 Epub); U.S. Pat. No. 6,656,730 and the like. For reviews of peptide-oligonucleotide conjugation chemistries, see also Tung et al., 2000, Bioconjugate Chem. 11:605-618; Zatsepin et al., 2005, Curr Pharm Des. 11(28):3639-3654; and Juliano, 2005, Curr Opin Mol. Ther. 7(2):132-136.

III. Cargo

The targeted DNA-based carrier, for instance, a DNA dendrimer, may be used to deliver any molecular or supramolecular cargo to a cell by contacting a cell with a composition comprising a DNA-based carrier, a targeting moiety and a cargo. One, or two or more different cargoes may be delivered by a targeted DNA-based carrier. Cargoes that can be delivered in accordance with the method of the invention include, but are not limited to, biologically active agents, including, but not limited to, therapeutic agents; imaging agents; and monitoring agents. A cargo may be an exogenous material or an endogenous material.

Biologically active agents include any molecule that induces an effect in a cell. Biologically active agents may be a protein, a nucleic acid, a small molecule, a carbohydrate, and a lipid. When the cargo is or comprises a nucleic acid, the nucleic acid may be a separate entity from the DNA-based carrier. In these embodiments, the DNA-based carrier is not itself the cargo. In other embodiments, the DNA-based carrier may itself comprise a nucleic acid cargo. Therapeutic agents include chemotherapeutic agents, anti-oncogenic agents, anti-angiogenic agents, tumor suppressor agents, anti-microbial agents, enzyme replacement agents, gene expression modulating agents and expression constructs comprising a nucleic acid encoding a therapeutic protein or nucleic acid. Therapeutic agents may be peptides, proteins (including enzymes, antibodies and peptidic hormones), ligands of cytoskeleton, nucleic acid, small molecules, non-peptidic hormones and the like. To increase affinity for the nucleus, agents may be conjugated to a nuclear localization sequence. Nucleic acid that may be delivered by the method of the invention include synthetic and natural nucleic acid material, including DNA, RNA, transposon DNA, antisense nucleic acids, dsRNA, siRNAs, transcription RNA, messenger RNA, ribosomal RNA, small nucleolar RNA, microRNA, ribozymes, plasmids, expression constructs, etc.

Modified nucleic acids may be used in the method of the invention. Non-limiting examples of such chemical modifications independently include without limitation phosphate backbone modification (e.g. phosphorothioate internucleotide linkages), nucleotide sugar modification (e.g., 2'-O-methyl nucleotides, 2'-O-allyl nucleotides, 2'-deoxy-2'-fluoro nucleotides, 2'-deoxyribonucleotides), nucleotide base modification (e.g., "universal base" containing nucleotides, 5-C-methyl nucleotides), and non-nucleotide modification (e.g., abasic nucleotides, inverted deoxyabasic residue) or a combination of these modifications. In addition, oligonucleotides having morpholino backbone structures (U.S. Pat. No. 5,034,506) or polyamide backbone structures (Nielsen et al., 1991, Science 254: 1497) may also be used. These and other chemical modifications can preserve biological activity of a nucleic acid in vivo while at the same time, dramatically increasing the serum stability, potency, duration of effect and/or specificity of these compounds. Nucleic acids containing modified internucleoside linkages may also be synthesized using reagents and methods that are well known in the art. For example, methods for synthesizing nucleic acids containing phosphonate phosphorothioate, phosphorodithioate, phosphoramidate methoxyethyl phosphoramidate, formacetal, thioformacetal, diisopropylsilyl, acetamidate, carbamate, dimethylene-sulfide ($-CH_2-S-CH_2$), dimethylene-sulfoxide ($-CH_2-SO-CH_2$), dimethylene-sulfone ($-CH_2-SO_2-CH_2$), 2'-O-alkyl, and 2'-deoxy-2'-fluoro phosphorothioate internucleoside linkages are well known in the art (see Uhlmann et al., 1990, Chem. Rev. 90:543-584; Schneider et al., 1990, Tetrahedron Lett. 31:335 and references cited therein).

The examples of oligonucleotide modifications described herein are not exhaustive and it is understood that the invention includes additional modifications of the oligonucleotides of the invention which modifications serve to enhance the therapeutic or other properties of the oligonucleotides without appreciable alteration of the basic sequence of the oligonucleotide. Similarly, protein cargoes may be modified as described elsewhere herein Imaging agents include contrast agents, such as ferrofluid-based MRI contrast agents and gadolinium agents for PET scans, fluorescein isothiocyanate and 6-TAMARA. Monitoring agents include reporter probes, biosensors, green fluorescent protein and the like. Reporter probes include photo-emitting compounds, such phosphors, radioactive moieties and fluorescent moieties, such as rare earth chelates (e.g., europium chelates), Texas Red, rhodamine, fluorescein, FITC, fluo-3, 5 hexadecanoyl fluorescein, Cy2, fluor X, Cy3, Cy3.5, Cy5, Cy5.5, Cy7, dansyl, phycocrytherin, phycocyanin, spectrum orange, spectrum green, and/or derivatives of any one or more of the above. Biosensors are molecules that detect and transmit information regarding a physiological change or process, for instance, by detecting the presence or change in the presence of a chemical. The information obtained by the biosensor typically activates a signal that is detected with a transducer. The transducer typically converts the biological response into an electrical signal. Examples of biosensors include enzymes, antibodies, DNA, receptors and regulator proteins used as recognition elements, which can be used either in whole cells or isolated and used independently (D'Souza, 2001, Biosensors and Bioelectronics 16:337-353).

In some embodiments, the cargo is linked to the DNA-based carrier. In some embodiments, where two or more different cargoes are to be delivered by a targeted DNA-based carrier, one cargo is linked to the DNA-based carrier while one or more other cargos are not linked. In some embodiments, all cargos are linked to the DNA-based carrier. In any of these embodiments, the composition may further comprise a secondary carrier. The targeting moiety may be linked to the secondary carrier in addition to, or in lieu of, the DNA-based carrier. The targeting moiety may be linked to the cargo in addition, or in lieu of, the DNA-based carrier. In some embodiments, a sequence of the DNA-based carrier may itself be the targeting moiety. Optionally, the DNA-based carrier is linked to the secondary carrier.

Linkage may be noncovalent or covalent. Covalent linkages include linkages susceptible to cleavage once internalized in a cell. Such linkages include pH-labile, photo-labile and radio-labile bonds and are well known in the art. Cargos may be linked to an oligonucleotide comprising a sequence that is substantially complementary to a binding arm to a sequence present in one of the binding arms on the surface of the DNA dendrimer or to a portion of single stranded sequence of any DNA-based carrier. The oligonucleotide may further comprise a nucleic acid cargo. The binding arm of a DNA dendrimer, or a portion of any DNA-based carrier, may also be designed to comprise a sequence complementary to a sequence in a known nucleic acid molecule (e.g., genomic DNA, cDNA, RNAs, plasmids, etc) in order to link a nucleic acid cargo directly to the DNA dendrimer. A binding arm, branch or the body of a DNA dendrimer, or a portion of any DNA-based carrier, may also be designed to comprise a sequence that is a cargo (e.g., a DNA oligonucleotide).

In some embodiments, the cargo is not linked to the DNA-based carrier. In these embodiments, a targeted DNA-based carrier binds to its target cell surface molecule, inducing formation of endocytic vesicles that passively incorporate a cargo present in the proximal extracellular milieu. A molecule that is incorporated into anendocytic vesicle is considered to have contacted the cell, without regard to whether there is physical contact between an exterior portion of the cell and the molecule. Alternatively, the targeting moiety is linked to the cargo, and the DNA-based carrier in the proximal extracellular milieu is passively incorporated into endocytic vesicles comprising the targeted cargo. As discussed elsewhere herein, it is believed that DNA-based carrier is capable of non-damaging permeation of the endosomal membrane, enabling the contents of the endosomal vesicle, including the cargo, to reach the cytosol, with reduced degradation, as compared to other delivery methods.

In some embodiments, the cargo is linked to the targeting moiety, or a cargo molecule may naturally comprise a targeting moiety, such as mannose-5-phosphate residues in an acid hydrolase. Such a targeted cargo may bind to the target cell surface molecule on a target cell and be incorporated into endosomal and lysosomal vesicles, but does not substantially get released to the cytosol. In contrast, administration of a DNA-based carrier with a targeted cargo facilitates the release of the cargo into the cytosol. DNA-based carrier in the proximal extracellular milieu of the targeted cargo bound to a cell surface molecule are expected to be passively incorporated into endocytic vesicles with the bound cargo. As described elsewhere herein, the DNA-based carrier is capable of non-damaging permeation of the endosomal membrane, facilitating release of the vesicle contents. Alternatively, a targeting moiety may also be linked to the DNA-based carrier. The targeting moiety may target the same or a different cell surface molecule on the target cell as the targeting moiety on the cargo, provided at least some cargo and DNA-based carrier are endocytosed in the same vesicle.

IV. Methods of Using Targeted DNA-Based Carrier

The invention provides a method of delivering a cargo to a cell. In one embodiment, the method is carried out by contacting a cell with a DNA-based carrier, a targeting moiety and a cargo or with a composition comprising a DNA-based carrier, a targeting moiety and a cargo. In another embodiment, the method is carried out by administering a DNA-based carrier, a targeting moiety and a cargo separately, or in any combination, either at the same time or in any given order in time.

The method of the invention can be used in any application requiring or involving the cellular targeting of a cargo. The methods may be used for diagnostic applications, research applications and therapeutic applications. The method may be carried out in vitro, ex vivo or in vivo. The method may be used for delivery to any cell type and any species of cell. As shown herein, DNA dendrimers carrying cargoes have been successfully targeted to a diversity of cell types, including endothelial cells, mesothelial cells and fibroblasts. Cells are preferably mammalian cells. Mammalian cells include, for instance, human, non-human primates, goat, sheep, horse, rat, mouse and rabbit cells. The method may be practiced with cells in culture, cells present within a tissue or cells within an individual. The method may be practiced with cells ex vivo, wherein the cells are subsequently returned to the individual.

The method may be practiced in some embodiments by administering a composition comprising a DNA-based carrier, a targeting moiety and a cargo to a cell or to an individual comprising the cell. In other embodiments, the three components are administered separately, in any order, or in any combination, to a cell or an individual, wherein they are intended to act in concert at the targeted cell. The three components may be administered in three separate administrations. Alternatively, components are administered in various combinations. For instance, cargo and DNA-based carrier may be administered separately from a targeting moiety. Similarly, cargo and a targeting moiety may be administered separately from the DNA-based carrier. Further, the DNA-based carrier and targeting moiety may be administered separately from the cargo. The separate administrations may occur substantially at the same time (e.g., within 2-4 hours of each other) or temporally proximal (e.g, within the same 24 hours). Alternatively, depending on the half-life and stability of the individual components in the system to which they are administered, administration of the components may be separated by greater periods of time, e.g., 30, 36 or more hours, 2, 3, 4 or more days, or 1, 2, 3 or more weeks, or longer.

A non-limiting example of practicing the method of the invention using separate components administered separately is as follows. A biotinylated antibody (targeting moiety) that specifically binds a cell surface molecule expressed in a specific disease is administered to a mammal first. After a period of time sufficient to substantially eliminate the unbound antibody from the mammal, an imaging agent (cargo) conjugated to streptavidin is administered, followed by administration of a DNA-based carrier, for instance, a DNA dendrimer. The imaging agent will accumulate in the disease tissue by binding to the biotinylated antibody bound to the disease tissue and will be internalized, along with DNA-based carrier proximal to the disease tissue, into endo-lysosomes. The DNA-based carrier facilitates release of the imaging agent to the cytosol, thereby minimizing degradation that would occur if the imaging agent remained in a lysosomal compartment. Thus, the imaging agent can accumulate intracellularly and permit sustained imaging monitoring. The skilled artisan will readily recognize variations of this embodiment and other applications, such as the use of a therapeutic agent as the cargo, which are included in the invention. Accordingly, the invention provides a method of delivering a cargo to a cell by administering a targeting moiety which targets a cell surface molecule on the cell, a cargo and a DNA-based carrier.

While the targeting moiety targets a cell surface molecule associated with an endocytic pathway, the invention contemplates the use of a composition comprising a DNA-based carrier, a cargo and a targeting moiety to deliver some or all of the cargo to the surface of a cell. That is, while some of the cargo is endocytosed, the cargo may also function locally and external to the cell. The targeted DNA-based carrier composition provides a way to locally concentrate the cargo at the cell surface. For instance, an imaging agent may be targeted to a cell using the composition of the invention and may be locally concentrated at the surface of a targeted cell, as well as being taken up by the cell.

The invention also enables binding and concentrating an endogenous material to a target cell. In this embodiment, a targeted DNA-based carrier further comprises a second moiety that specifically binds to an endogenous material present, stably or transiently, in the extracellular milieu of the target cell. The targeted DNA-based carrier binds to the target cell and, by means of the second moiety, binds to the endogenous material, thus locally concentrating the endogenous material at the target cell. Preferably, the endogenous material is endocytosed with the DNA-based carrier. The endogenous material may be any material originating in the individual, including, but not limited to, a protein, an enzyme, an antibody, a lipid, a lipoprotein or a cell. As a non-limiting example, a DNA-based carrier is linked to a first antibody (targeting moiety) that targets an endothelial cell surface molecule, e.g., ICAM-1 or PECAM-1, and to a second antibody that specifically binds a protein in the blood. The targeted DNA-based carrier is administered intravenously. The targeted DNA-based carrier binds to an endothelial cell and "captures" the blood protein, locally concentrating it proximal to the endothelial cell. Endocytosis of the DNA-based carrier carries the blood protein into the endosome, with delivery to the cytosol, facilitated by the DNA-based carrier.

In one embodiment of the method of the invention, the cargo is a therapeutic agent, and the method is used to alleviate a disorder or disease or provide a prophylactic treatment for a disorder or disease. The method is carried out by administering a composition comprising a DNA-based carrier, a targeting moiety and a therapeutic agent cargo to an individual in need thereof. By avoiding or limiting lysosomal delivery and degradation of a cargo, thereby increasing the effective concentration of cargo delivered, the invention is contemplated to enable the reduction in dose of a therapeutic, compared to prior art delivery methods. Reducing the dose also advantageously reduces the risk of potential side effects. In some embodiments, the therapeutic agent is a polypeptide or a small molecule drug. In other embodiments, the therapeutic agent comprises nucleic acid. The therapeutic molecule may be any therapeutic molecule that can be encoded in a polynucleotide. Non-limiting examples of types of therapeutic molecules that can be encoded in an expression cassette in the instant invention include, but are not limited to, polypeptide enzymes, cytokines, hormones, antibodies, such as intrabodies or scFvs, a suicide gene, such as HSV-TK, a molecule that inhibits vascularization, a molecule that increases vascularization, tumor suppressors, such as p53 and p21, pro-apoptotic molecules, such as TRAIL, transcription factors, receptors, ligands, immunogenic molecules, anti-proliferative molecules, agonists, antagonists, anti-inflammatory molecules, antibiotics, antidepressants, prodrugs, anti-hypertensives, anti-oxidants, and the like. The therapeutic molecule comprising a nucleic acid may be a nucleic acid that modulates the expression in vivo of a gene. Such nucleic acids include antisense molecules, siRNA and ribozymes.

Thus, the method of the invention provides a novel therapeutic approach to a broad spectrum of diseases and conditions, including cancer or cancerous disease, infectious disease, ocular disease, cardiovascular disease, neurological disease, prion disease, inflammatory disease, autoimmune disease, metabolic disease, genetic disease, pulmonary disease, renal disease, liver disease, mitochondrial disease, endocrine disease, reproduction related diseases and conditions, graft vs host disease, and any other indications that can respond to the level of an expressed gene product in a cell or individual.

The art is replete with exemplary molecules and associated diseases or disorders where a patient may benefit from the expression or inhibition of expression of one or more molecules. For instance, an assessment of expression changes in gene families in a variety of human cancers has been pursued (U.S. Pat. Appl. Pub. No. 20060168670). In addition, tissue-specific expression levels have been mapped for thousands of genes through expression profiling (Alon et al., 1999, Proc. Natl. Acad. Sci. USA 96:6745-50; Iyer et al., 1999, Science 283: 83-87; Khan et al., 1998, Cancer Res. 58: 5009-13; Lee et al., 1999, Science 285:1390-93; Wang et al., 1999, Gene 229:101-08; and Whitney et al., 1999, Ann. Neurol. 46:42). Thus, the skilled artisan is able to select molecules useful in the practice of the present invention without undue experimentation.

In some preferred embodiments, DNA dendrimers are targeted to CAM-expressing cells and in particular, ICAM-1- or PECAM-1-expressing cells. ICAM-1 is expressed on epithelial cells that line diverse cavities in the body. Thus, the invention provides a method of delivering a cargo to an epithelial cell using ICAM-1-targeted DNA dendrimers. PECAM-1 and ICAM-1 are highly expressed by endothelial cells lining the luminal surface of blood and lymphatic vessels. Therefore, the method of the invention is also useful for delivering a cargo to endothelial cells in vascularized organs, including kidney, brain, spleen, liver, heart and lungs using ICAM-1 or PECAM-1 targeted DNA dendrimers, for treatment of diverse disease and disorder conditions involving these organs, including but not limited to cardiovascular, cerebrovascular, hematological, hepatic, renal, pulmonary and other diseases and/or disorders having pathologies that involve endothelial cells. In an embodiment, the invention provides a method of treating vascular oxidative stress by administering to an individual a targeted DNA-based carrier, and a cargo, wherein the cargo is an antioxidant enzyme or a nucleic acid encoding an antioxidant enzyme and wherein the DNA-based carrier is targeted to an endothelial cell. An exemplary antioxidant enzyme is catalase. In another embodiment, the invention provides a method of treating genetic diseases due to genetic defects of hydrolases, such as the lysosomal storage disorders, by administering to an individual a targeted DNA-based carrier, and a cargo, wherein the cargo is a nucleic acid encoding the hydrolase which is genetically deficient in the individual. In another embodiment, the invention provides a method of treating cancer-related diseases, by administering to an individual a targeted DNA-based carrier, and a cargo, wherein the cargo is a siRNA or a microRNA with capacity to modulate the expression of genes associated to the cancer condition. nucleic acid encoding the hydrolase which is genetically deficient in the individual.

ICAM-1 is also expressed on mesothelial cells lining lung pleura and diverse types of malignant cells. Therefore, the method of invention is also useful for delivering a cargo to these cells. Due to diversity of ICAM-1-expressing cells, as described above, and their involvement in pathogenesis of diverse diseases and disorders, ICAM-targeted dendrimers can be used for diagnosis and treatment of diverse syndromes including but not limited to inflammatory, metabolic, necrotic, ischemic, malignant growth and other syndromes involved in diseases and disorders. Since CAM-mediated endocytosis is independent of clathrin and caveolae, this embodiment is useful for delivering therapeutics to cells in pathologies involving reduced or disrupted clathrin- or caveolae-dependent endocytosis. Examples of such diseases of disorders include, but are not restricted to, lysosomal storage disorders, Dent's disease, and chronic granulomatosis disease (Grassme, et al., 1997, Cell 91: 605-15; Dhami et al., 2004, J Biol. Chem. 279: 1526-32; Dermaut et al., 2005, J. Cell Biol. 170: 127-39; Monroy et al., 2002, Bone 30: 352-9; Goebel et al., 1992, Ophthalmic Res 24: 103-9; Wang et al., 2000, Hum Mol Genet. 9(20): 2937-45; Geiszt, 2001, J Leukoc Biol 69(2):191-196). In an embodiment, the invention provides a method of treating a lysosomal storage disorder by administering to an individual a targeted DNA-based carrier and a cargo selected from the group consisting of acid sphingomyelinase and a nucleic acid encoding acid sphingomyelinase.

In some preferred embodiments, a DNA dendrimer is targeted to cells expressing transferrin receptor or mannose-6-phosphate receptor. Transferrin receptor and mannose-6-phosphate receptor are comparatively ubiquitous molecules, and are enriched in certain cell types in the body. In particular, transferrin receptor has been shown to be predominantly expressed in the blood brain barrier and certain tumor vasculatures. Mannose-6-phosphate receptor is particularly abundant in cells of the reticulo-endothelial system and immune cells. Thus, the invention provides a method of delivering a cargo to these tissues in the body.

The invention also provides compositions, including pharmaceutical compositions, to practice the methods of the invention, the compositions comprising a DNA-based carrier, a targeting moiety and a cargo. Preferably, the DNA-based carrier is a DNA dendrimer. In therapeutic or diagnostic applications, the composition optionally further comprises a pharmaceutically-acceptable carrier. As used herein, the term "pharmaceutically-acceptable carrier" means a chemical composition with which a targeted DNA-based carrier in accordance with the invention may be combined and which, following the combination, can be used to administer a cargo to a mammal.

Although the description of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

The pharmaceutical compositions useful for practicing the invention may be administered to deliver a dose of a cargo between 1 ng/kg/day and 100 mg/kg/day. In one embodiment, the invention envisions administration of a dose which results in a concentration of a cargo between 1 µM and 10 µM in a mammal.

Typically, dosages which may be administered in a method of the invention to an animal, preferably a human, range in amount from 0.5 µg to about 50 mg per kilogram of body weight of the animal. While the precise dosage administered will vary depending upon any number of factors, including but not limited to, the type of animal and type of disease state being treated, the age of the animal and the route of administration. Preferably, the dosage of a cargo will vary from about 1 µg to about 10 mg per kilogram of body weight of the animal. More preferably, the dosage will vary from about 3 µg to about 1 mg per kilogram of body weight of the animal.

With regard to the quantity of DNA-based carrier administered, the amount may vary from 1 to 1,000,000 molecules of a targeting moiety and/or molecule of a cargo per DNA-based carrier, depending on the specific activity, molecular mass, and/or affinity of the given cargo, targeting moiety and carrier. Doses for in vitro administrations, such as in tissue culture applications, may vary from 0.1 to 1,000,000 nanograms of DNA-based carrier per 100,000 cells. Doses for in vivo administration may vary from 10 nanograms to 100 milligrams of DNA-based carrier per kilogram of body weight. The invention, however, should not be construed as limited to these ranges.

The composition may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc.

The formulations of the pharmaceutical compositions described herein may be prepared by any method known or hereafter developed in the art of pharmacology. In general, such preparatory methods include the step of bringing the active ingredient (e.g., the cargo) and a targeted DNA-based carrier, and a pharmaceutically-acceptable carrier or one or more other accessory ingredients, and then, if necessary or desirable, shaping or packaging the product into a desired single- or multi-dose unit. The cargo may be present in the pharmaceutical composition in the form of a physiologically acceptable ester or salt, such as in combination with a physiologically acceptable cation or anion, as is well known in the art.

As used herein, the term "physiologically acceptable" ester or salt means an ester or salt form of the active ingredient which is compatible with any other ingredients of the pharmaceutical composition, which is not deleterious to the subject to which the composition is to be administered.

For oligonucleotides and nucleic acids, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

Pharmaceutical compositions that are useful in the methods of the invention may be prepared, packaged, or sold in formulations suitable for parenteral, ophthalmic, topical, pulmonary, buccal, intranasal, oral, rectal, vaginal, or another route of administration. In addition to the targeted nucleic acid and pharmaceutically-acceptable carrier, the pharmaceutical compositions may contain other ingredients known to enhance and facilitate drug administration.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the targeted DNA-based carrier, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient and targeted DNA-based carrier.

In addition to the active ingredient, a pharmaceutical composition of the invention may further comprise one or more additional pharmaceutically active agents.

Controlled- or sustained-release formulations of a pharmaceutical composition of the invention may be made using conventional technology.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intravenous, intraocular, intravitreal, subcutaneous, intraperitoneal, intramuscular, intrasternal injection, intratumoral, and kidney dialytic infusion techniques. Parenteral administration is particularly preferred with ICAM-1-, PECAM-1-, TrfR-, and M6PR-targeted DNA-based carriers, preferably DNA dendrimers.

Formulations of a pharmaceutical composition suitable for parenteral administration comprise the active ingredient and targeted DNA-based carrier combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient and targeted DNA-based carrier is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient and targeted DNA-based carrier, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient and targeted DNA-based carrier in microcrystalline form, in a liposomal preparation, in microbubbles for ultrasound-released delivery, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for pulmonary administration via the buccal cavity. Such formulations provide the active ingredient and targeted DNA-based carrier in the form of droplets of a solution or suspension. Such formulations may be prepared, packaged, or sold as aqueous or dilute alcoholic solutions or suspensions, optionally sterile, comprising the active ingredient and targeted DNA-based carrier, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter of about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and targeted DNA-based carrier and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient and targeted DNA-based carrier, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient and targeted DNA-based carrier, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient and targeted DNA-based carrier. Such powdered, aerosolized, or aerosolized formulations, when dispersed, preferably have an average particle or droplet size in the range of about 200 nanometers, and may further comprise one or more of the additional ingredients described herein.

A pharmaceutical composition of the invention may be prepared, packaged, or sold in a formulation suitable for ophthalmic administration. Such formulations may, for example, be in the form of eye drops including, for example, a 0.1-1.0% (w/w) solution or suspension of the active ingredient and targeted DNA-based carrier in an aqueous or oily liquid carrier. Such drops may further comprise buffering agents, salts, or one or more other of the additional ingredients described herein. Other ophthalmically-administrable formulations which are useful include those which comprise the active ingredient and targeted DNA-based carrier in microcrystalline form or in a liposomal preparation, provided the receptor-binding moiety of the targeting molecule is accessible to target delivery to the cognate receptor.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Remington's Pharmaceutical Sciences (1985, Genaro, ed., Mack Publishing Co., Easton, Pa.), which is incorporated herein by reference.

V. Kits

The invention also provides kits useful for carrying out a method of the invention. The kit comprises a composition comprising a targeted DNA-based carrier and an instructional material for using the targeted DNA-based carrier to delivery a cargo to a cell. In preferred embodiments of the kit, the DNA-based carrier is from the group consisting of a DNA dendrimer, a double-stranded DNA, a single-stranded DNA, a single-stranded hairpin DNA and multimers thereof. In one embodiment, the targeting moiety of the targeted DNA-based carrier is an antibody to a cell adhesion molecule. In a preferred embodiment, the targeting moiety is an antibody to ICAM-1 or to PECAM-1. In another embodiment, the targeting moiety is an antibody to one of transferrin receptor and mannose-6-phosphate receptor. In one embodiment, the targeting moiety is linked directly to the DNA-based carrier. In an embodiment, the DNA-based carrier is a dendrimer. In one embodiment, the targeting moiety is linked to an oligonucleotide comprising a sequence substantially complementary to a binding arm of the DNA dendrimer. In some embodiments, the kit further comprises a cargo. Optionally, the composition in the kit further comprises a secondary carrier selected from the group consisting of a liposome, a non-DNA dendrimer, a polymer carrier, a microbubble, a paramagnetic particle, a ferromagnetic particle, a self-assembled polymer, a polymersome, a filomicelle, an albumin particle, and a lipoprotein. Optionally, the kit further comprises an applicator. The instructional material in each kit simply embody the disclosure provided herein.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Experimental Example 1

Targeting Beads with Anti-ICAM Antibody

Anti-ICAM complexes ("anti-ICAM/Bds") were prepared by surface absorption of monoclonal rat ant-mouse ICAM-1 antibody (clone YN1; Jevnikar et al., 1990, Kidney Int. 38:417:425) onto 100 nm polystyrene beads (Polysciences Inc., Warrington, Pa.) having a diameter of about 170 nm. These beads have been shown in the art to be internalized by cells in culture. Anti-ICAM/Bds (~1.3 mg antibody and $5.6 \times 1011$ µm$^2$ total particle surface per kg of body weight) were injected intravenously in ketamine/xylazine anesthetized control C57Bl/6 mice. Three (3) hours post-injection, organs were perfused with fixative, harvested and processed for ultrastructural analysis by transmission electron microscopy.

Figure 1B:
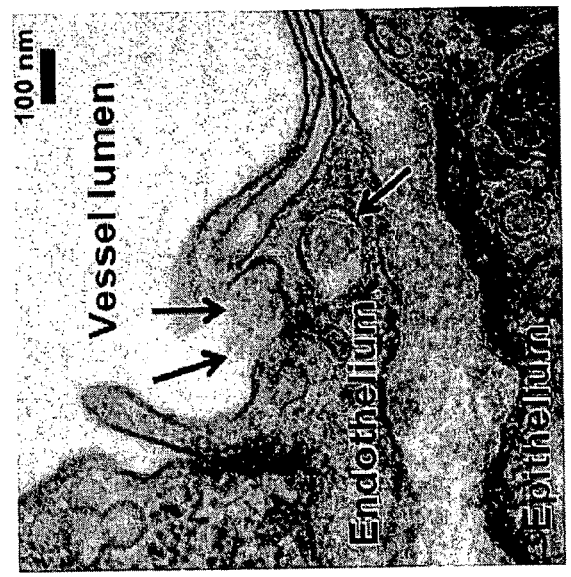

Anti-ICAM/Bds were clearly detected bound to the plasma membrane of cells (e.g., endothelial cells in the pulmonary vasculature) and being internalized in endocytic vesicles (FIG. 1A). The vesicles were distinct from clathrin- and caveolar-like compartments, and were smaller in size than classical macropinosomes or phagosomes vesicles. Moreover, anti-ICAM/Bds were detected within electron dense compartments (FIG. 1B), demonstrating that ICAM-1 targeting induces endocytosis followed by endo-lysosomal trafficking in laboratory animals. These results demonstrate for the first time that ICAM-1-targeting can successfully deliver moderately large (about 200 nm) delivery systems into these compartments in vivo.

Experimental Example 2

Targeting DNA Dendrimers with Anti-ICAM Antibody

Figures 2A, 2B:
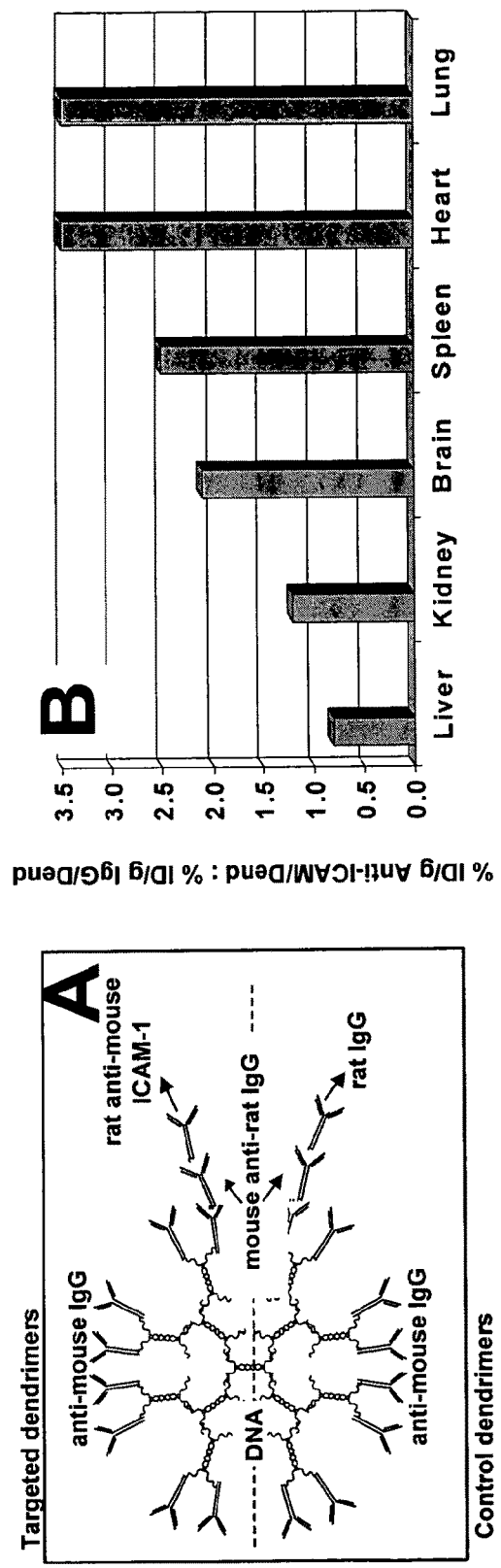
FIGS. 2A-2D are a series of images of schematic drawings, a graph and representative micrograph images related to anti-ICAM-targeted DNA dendrimers.

To test anti-ICAM targeting of a DNA dendrimer, 3DNA® dendrimers conjugated to anti-mouse IgG (Genisphere®, Hatfield, Pa.) were indirectly coupled to anti-ICAM antibodies (anti-ICAM/Dend). First, anti-mouse IgG-conjugated dendrimers were incubated with $^{125}$I mouse anti-rat IgG (Jackson Immunoresearch Laboratories, Inc., West Grove, Pa.), followed by incubation with either control rat IgG (Jackon Immunoresearch Laboratories, Inc) (IgG/Dend) as a negative control or clone YN1 rat anti-mouse ICAM (anti-ICAM/Dend) as the targeted complex. See FIG. 2A. Dendrimer preparations containing 40 µg/Kg body weight of DNA dendrimer and 2 mg/Kg body weight control IgG or targeting anti-ICAM antibody were injected intravenously into anesthesized C57Bl/6 male mice. The organ distribution of the targeted and control dendrimers was determined in a gamma counter 30 minutes post-injection. As shown in FIG. 2B, ICAM-targeted dendrimers exhibited targeting in vivo to liver and kidney, and specific uptake over control dendrimers (IgG/Dend) in brain, spleen, heart, and lung.

Figures 2C, 2D:
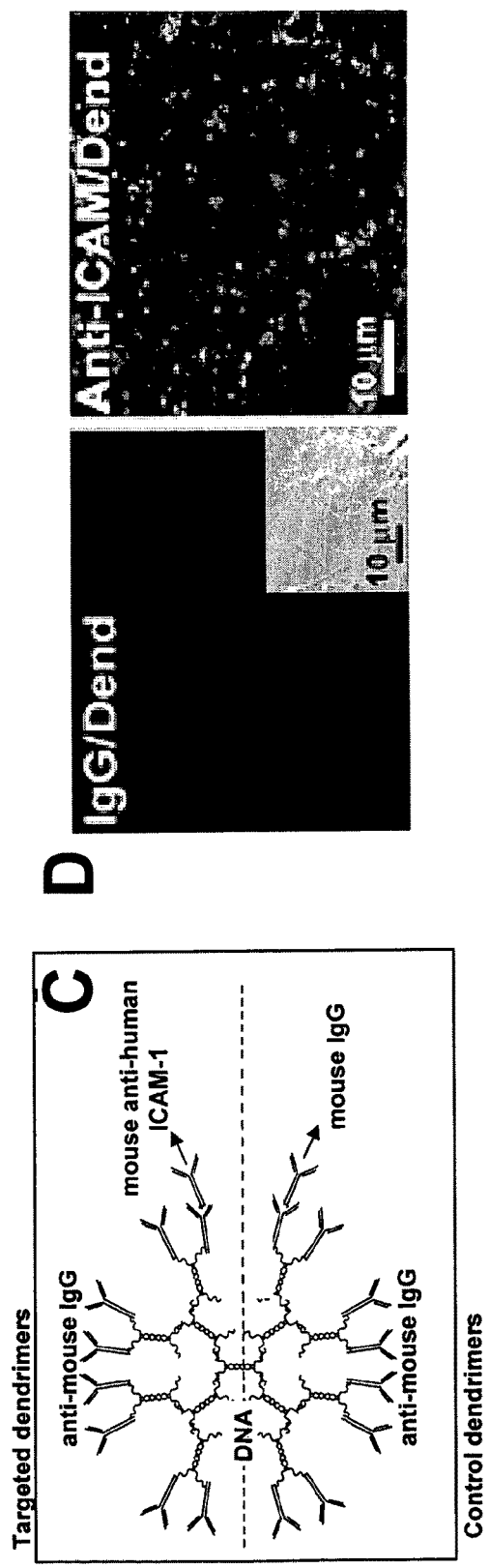

To assess specific cellular binding, anti-mouse IgG-conjugated dendrimers were coupled to either FITC mouse IgG (Jackson Immunoresearch Laboratories, Inc.) or mouse anti-human ICAM-1 (clone R6.5; Marlin et al., 1987, Cell 51:813-819) covalently conjugated to FITC using Fluoreporter® protein labeling kit (Invitrogen-Molecular Probes, Eugene, Oreg.) (FIG. 2C). Dendrimers samples containing 0.25 ng/ml dendrimer and 10 ng/ml anti-ICAM were incubated for 1 hour with human umbilical vein endothelial cells (HUVEC) in culture at 4° C. After incubation, cells were washed to remove non-bound dendrimers. Cells were then fixed and analyzed by fluorescent and phase-contrast microscopy. It was observed that anti-ICAM/Dend, but not control IgG/Dend, bound specifically to HUVEC (FIG. 2D).

Experimental Example 3

Intracellular Delivery of DNA Dendrimers Targeted to Classical vs Non-Classical Endocytic Pathways in Various Cells Types The ability of HUVEC activated with TNF-α (10 ng/ml) to internalize anti-ICAM/Dend was tested at 4° C., a temperature that precludes endocytosis, and at 37° C. for 1 hour. After incubation, the cells were washed and nuclei were stained with DAP1. Non-internalized dendrimers were stained with a secondary antibody labeled in red. Thus, surface-bound dendrimers were detected as yellow color and internalized dendrimers, detected as green color. The cells were analyzed by fluorescence microscopy.

Figure 3A:
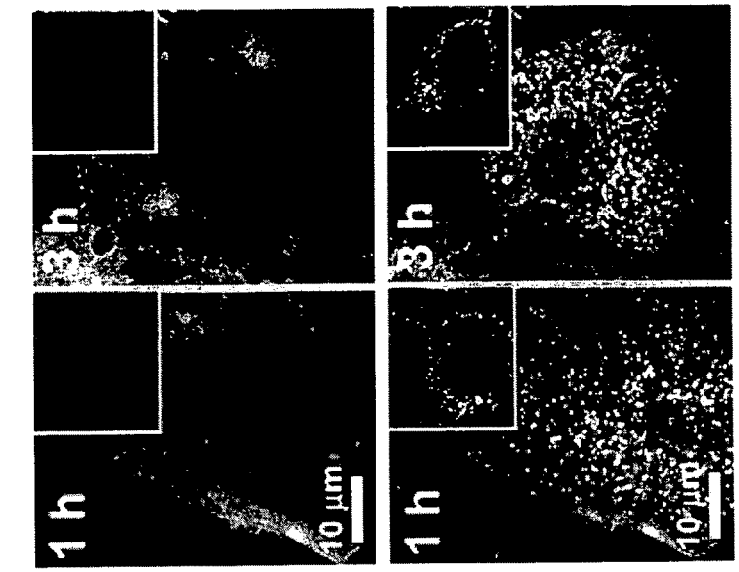
FIGS. 3A-3D are a series of representative fluorescent images of cells incubated with anti-ICAM-1 targeted dendrimers under different conditions.
Figure 3B:
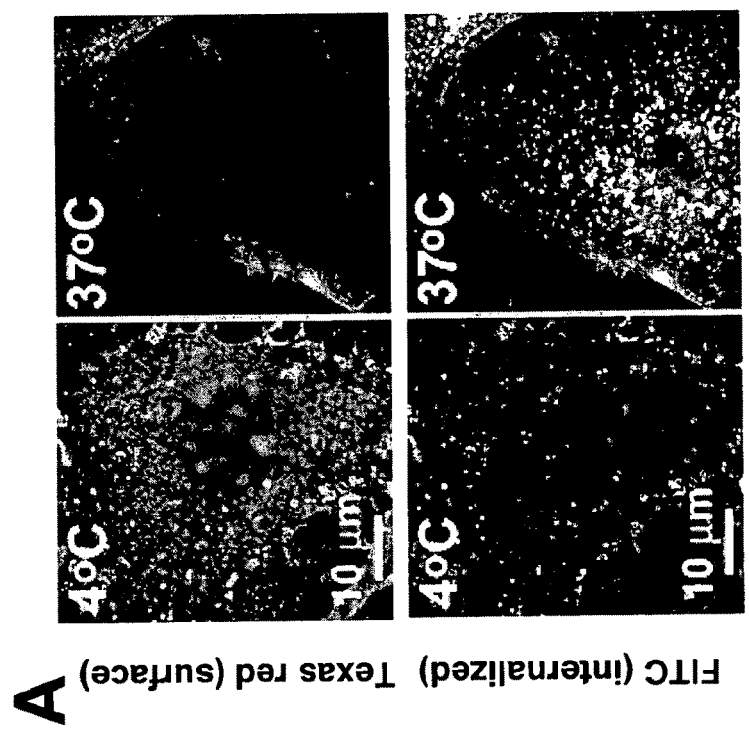

Anti-ICAM/Dend were internalized by HUVEC at 37° C. but not at 4° C. (FIG. 3A), indicating uptake by an energy-dependent mechanism. These data also suggest that uptake does not involve permeation of the plasma membrane. However, in contrast to anti-ICAM/Bds, which trafficked to endosomes and lysosomes located at the perinuclear region of the cell (see punctate staining in insets in FIG. 3B), internalized anti-ICAM/Dend appeared scattered throughout the cytosol.

PECAM-1 is another cell adhesion molecule associated with non-classical, CAM-mediated endocytosis. HUVEC were incubated with anti-PECAM-1/Dend for 3 hours at 37° C. As with anti-ICAM/Dend, anti-PECAM-1/Dend appeared scattered throughout the cytosol (FIG. 3C, right panel), indicating their uptake and internalization.

Figures 3C, 3D:
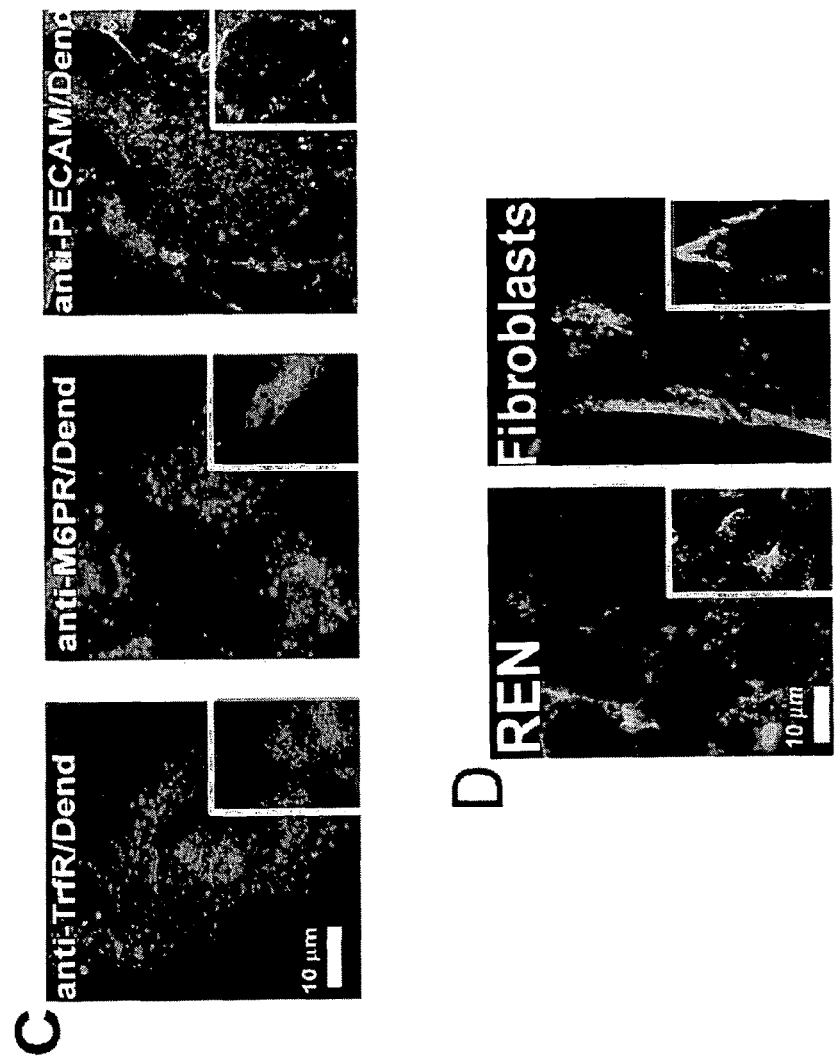

To explore targeting of DNA dendrimers to cell surface molecules associated with classical endocytosis, in particular, clathrin-mediated endocytosis, dendrimers targeted to transferrin receptor (anti-TrfR/Dend) and to mannose-6-phosphate receptor (anti-M6PR/Dend) were prepared as described in Example 2. HUVEC were incubated with anti-TrfR/Dend or anti-M6PR/Dend for 3 hours at 37° C. As observed for the CAM-targeted DNA dendrimers, these targeted dendrimers appeared scattered throughout the cytosol (FIG. 3C, left and middle panels). These data support the universal application of targeting DNA-based carriers, particularly DNA dendrimers, to any type of cell surface molecule which is associated with endocytotic internalization both by classical endocytosis pathways and non-classical endocytosis pathways.

To explore internalization of targeted DNA-based carriers with cell types other than endothelial, REN mesothelioma cancer cells and skin fibroblasts were incubated with anti-ICAM/Dend for 3 hours at 37° C. Representative images are shown in FIG. 3D, which show the targeting and internalization of targeted DNA dendrimers to non-endothelial cells. This data further supports the universal application to any cell type comprising a cell surface molecule associated with endocytosis.

When using anti-mouse IgG that recognizes only the Fc portion, the bound mouse IgG is expected to largely be oriented such that the antigen binding sites are extending toward the exterior of the dendrimer particle. When using anti-mouse IgG that recognizes both the Fc and the heavy and light chain (H&L) portions of the mouse IgG, one expects that binding of mouse IgG will result in a variety of orientations, not all of which are expected to be favorable for binding to the cell surface target. To examine whether dendrimers with the latter type of anti-mouse IgG could be used in the invention, anti-ICAM/Dend were prepared using dendrimers having anti-mouse IgG that recognizes both the Fc and the H&L portion of the targeting moiety antibody. As shown in the insets of FIGS. 3C and 3D, good targeting and internalization were observed with these dendrimers as well.

Experimental Example 4

Cargo Delivery with Anti-ICAM Targeted DNA Dendrimers

To assess whether cargoes co-internalized with anti-ICAM/Dend could escape from endo-lysosomal compartments, activated HUVEC were incubated with media containing 2 mg/ml Texas Red dextran (a sugar polymer of 10,000 Da that is a fluid-phase marker) and concomitantly with either anti-ICAM/Dend (0.25 ng/ml dendrimer and 10 ng/ml anti-ICAM) or control anti-ICAM-coupled polystyrene beads (anti-ICAM/Bds; $4.55 \times 10^{10}$ beads/ml and 5 ng/ml anti-ICAM) for 15 minutes at 37° C. to permit co-internalization of dextran and dendrimers or beads within the same vesicular compartments. The cells were then washed and incubated at 37° C. for an additional time up to 3 hours, then fixed and analyzed by fluorescence microscopy to track poration of vesicles and endosomal escape of dextran to the cytosol. Texas Red Dextran was observed to remain contained within endo-lysosomal vesicles for at least 5 hours when internalized with anti-ICAM/Bds (FIG. 4A, top images). In notable contrast, dextran disappeared from these vesicles and appeared in the cytosol when internalized with anti-ICAM/Dend (FIG. 4A, bottom images). These data indicate that anti-ICAM/Dend, but not anti-ICAM/Bds, provide cytosolic delivery of internalized materials.

In another series of experiments, activated HUVEC were incubated at 37° C. for varying periods of time with media containing either anti-ICAM/Dend or control anti-ICAM/Bds along with 1 μm ethidium homodimer-1 as cargo. Ethidium is an intercalating agent, which labels nuclear DNA if freed into the cytosol. Cells incubated at 4° C. served as a control for plasma membrane integrity, and cells permeabilized with 0.2% Triton X-100 served as a control for nuclear accessibility. Anti-ICAM/Bds and anti-ICAM/Dend provided different patterns of intracellular distribution of ethidium. Ethidium exhibited nuclear localization only when internalized with anti-ICAM/Dend (FIG. 4B). Similarly, when the cargo was a protein having an affinity for the nucleus (albumin conjugated to a nuclear localization sequence peptide), nuclear localization of the cargo was only detected with anti-ICAM/Dend (FIG. 5B).

A similar course of experiments was performed using a cargo that labels cytosolic F-actin. Phalloidin, a bicyclic heptapeptide, is a mushroom toxin that tightly binds actin if released into the cytosol. When the cargo was biotinylated phalloidin, cytosolic filamentous actin was labeled only when phalloidin was internalized with anti-ICAM/Dend (FIG. 5A). Thus, cytosolic delivery of cargoes by anti ICAM/Dend also provides accessibility to large structures, such as the intracellular cytoskeleton. Furthermore, incubation of cells at 4° C. with anti-ICAM/Dend did not result in labeling of these intracellular structures (cytosolic or nuclear) by the substances described above, indicating that anti-ICAM/Dend release cargoes into the cytosol across endosomal membranes (but not the plasma membrane) in an energy-dependent process.

Experimental Example 5

Functional Protein Transduction with Anti-ICAM/Dend

To assess intracellular delivery of a protein, activated HUVEC were incubated at 37° C. for 1 hour with control media or with media containing either anti-ICAM/Dend or control anti-ICAM/Bds along with the anti-oxidant enzyme catalase, washed and incubated for additional 2 hours at 37° C. to favor cytosolic escape of catalase (by ICAM/Dend) or its lysosomal degradation (anti-ICAM/Bds). Cells were then incubated for 16 hours with a 50 μM $H_2O_2$ solution and then washed. Cell viability was estimated by fluorescence microscopy analysis of cells stained with 0.1 μM calcein (which stains live cells in green) and 1 μM ethidium homodimer-1 (which stains dead cells in red).

Figure 6A:
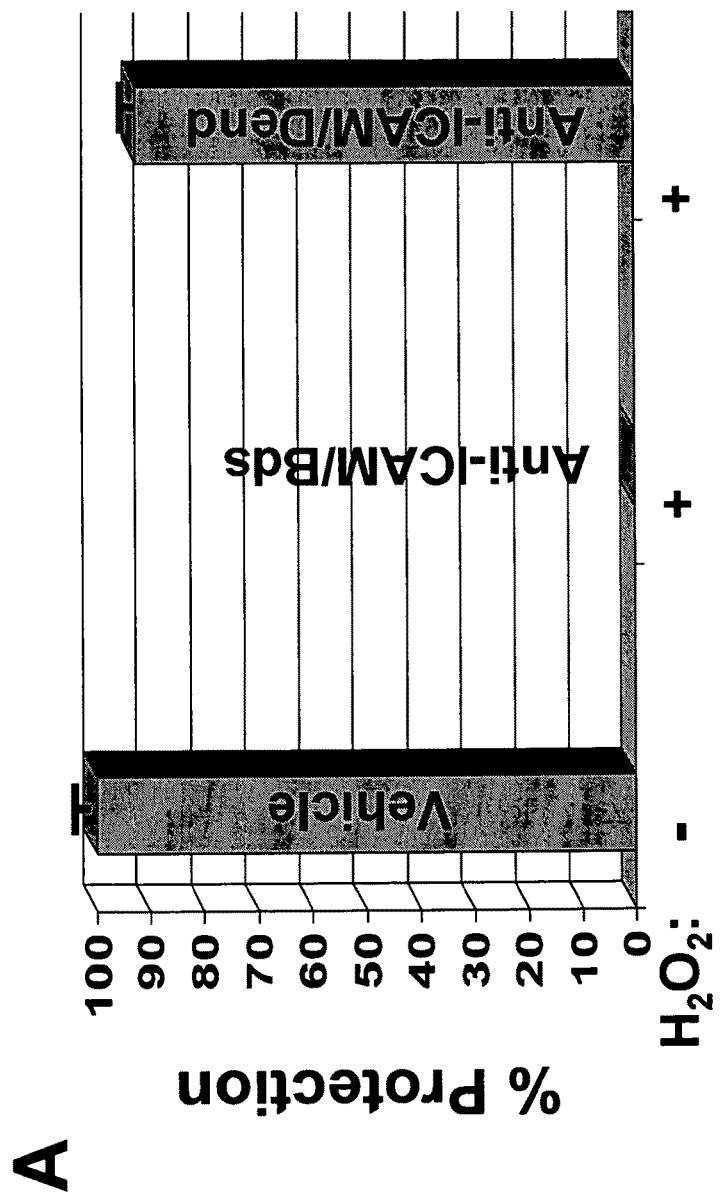
FIGS. 6A-6C are a series of images depicting data regarding functional protein transduction and plasmid transfection using anti-ICAM targeted DNA dendrimers.

When catalase was delivered with anti-ICAM/Bds, protection against $H_2O_2$-induced oxidative injury was gone 3 hours after internalization. It is believed that the loss in protection is due to lysosomal delivery and proteolytic degradation of the antioxidant enzyme, which has been observed in other systems (Muro et al., 2003, Am J Physiol Cell Physiol. 285(5):C1339-47). In notable contrast, catalase delivered with anti-ICAM/Dend protected cells for at least 16 hours against injury induced by $H_2O_2$ added to the cells 3 hours after dendrimer internalization (FIG. 6A). While not wishing to be bound by theory, it is believed that catalase internalized with anti-ICAM/Dend was delivered to the cytosol, which thus protects the enzyme from lysosomal degradation, thereby prolonging its protective activity.

Experimental Example 6

Plasmid Transfection with Anti-ICAM/Dend

To assess intracellular delivery of nucleic acid, activated HUVEC were incubated at 37° C. for 5 hours with media containing anti-ICAM/Dend along with a plasmid codifying for Rac-EGFP protein. Controls included cells incubated with naked plasmid or with plasmid and anti-ICAM/Bds. Forty-eight (48) hours later, the cells were washed and analyzed by phase-contrast and fluorescence microscopy to estimate transfection and expression of Rac-EGFP.

Figure 6B:
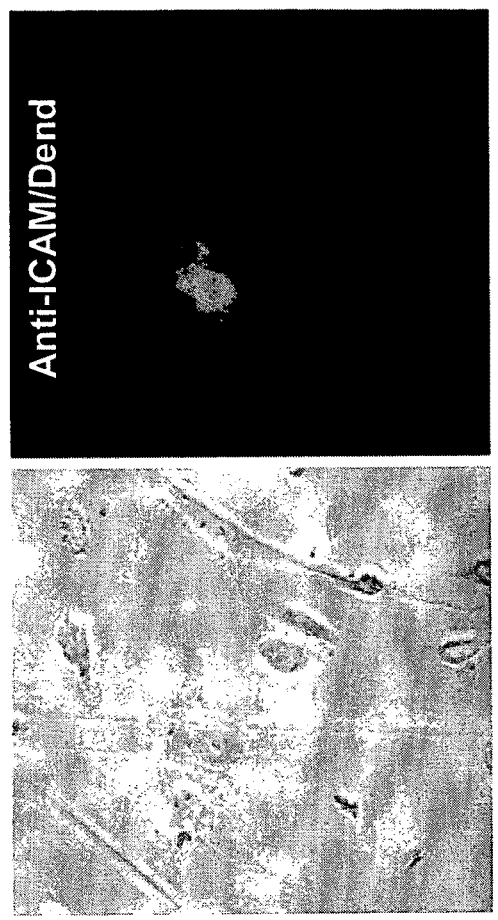
Figure 6C:
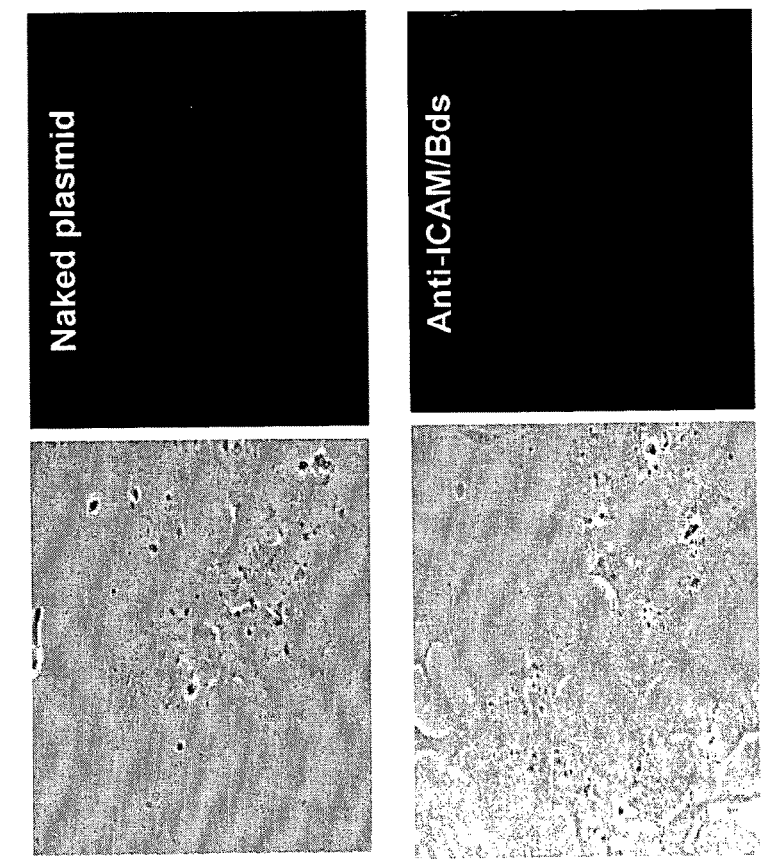

Cells incubated with naked plasmid or plasmid and anti-ICAM/Bds were not transfected (FIG. 6C). In contrast, HUVEC cells incubated with plasmid and anti-ICAM/Dend were transfected (FIG. 6B). Therefore, cytosolic delivery by anti-ICAM/Dend enables cargoes which need nuclear localization to be functional, such as genetic material, to reach the nucleus.

Experimental Example 7

Secondary Effects of Anti-ICAM Targeted DNA Dendrimers on Cells

Figures 7A, 7B:
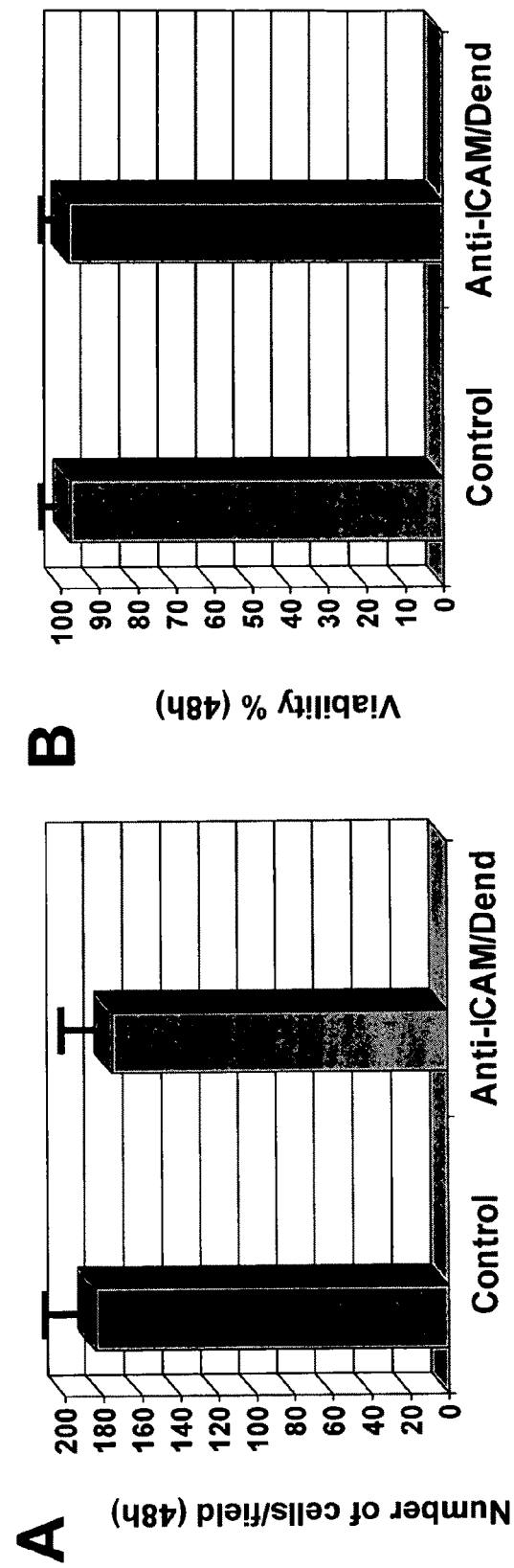
FIGS. 7A and 7B are a series of bar graphs depicting data regarding secondary effects of anti-ICAM targeted DNA dendrimers on cells.

To assess the effect of anti-ICAM targeted DNA dendrimers on cells, activated HUVEC were incubated either with control media or with media containing anti-ICAM/Dend at 37° C. for 5 hours. The cells were then washed, incubated for an additional 48 hours, stained with 0.1 μM calcein and 1 μM ethidium homodimer-1, and analyzed by phase-contrast and fluorescence microscopy to estimate the number of cells (FIG. 7A) and their viability (FIG. 7B). Anti-ICAM/Dend did not show evidence of monolayer disruption or cytotoxicity, even when tested 48 hours after cellular internalization in saturating amounts. Thus, anti-ICAM/Dend do not appear to have adverse secondary effects on cells.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A composition comprising
   a DNA dendrimer,
   a cargo which is a biologically active agent whose action is required in the cytosol or other intracellular compartment which the cargo cannot access by itself,
   and a targeting moiety which is a polypeptide which binds to a cell surface molecule,
   wherein said composition provides cytosolic delivery of the cargo without the need for other means to permeate or disrupt the cell membrane.

2. The composition of claim 1, wherein said targeting moiety is linked to said DNA dendrimer.

3. The composition of claim 1, wherein said cargo is linked to said DNA dendrimer.

4. The composition of claim 1, further comprising a secondary carrier linked to said DNA dendrimer, wherein the secondary carrier is polyethylene glycol (PEG).

5. The composition of claim 4, wherein said targeting moiety is linked to said secondary carrier.

6. The composition of claim 1, wherein said cell surface molecule is selected from the group consisting of intercellular adhesion molecule (ICAM), ICAM-1, platelet-endothelial cell adhesion molecule (PECAM), PECAM-1, activated leukocyte cell adhesion molecule (ALCAM), B-35 lymphocyte cell adhesion molecule (BL-CAM), vascular cell adhesion molecule (VCAM), selectins, mucosal vascular addressin cell adhesion molecule (MAdCAM), CD44, LFA2, LFA-3, basigin, mannose-6-phosphate receptor, and transferrin receptor.

7. A pharmaceutical composition comprising a composition of claim 1 and a pharmaceutically-acceptable excipient.

8. The composition of claim 1, wherein said polypeptide is an antibody selected from the group consisting of a monoclonal antibody, a humanized antibody, a synthetic antibody, single chain variable fragment (scFV), a heavy chain antibody, and a biologically active fragment of an antibody, wherein the biologically active fragment is a Fab fragment, a F(ab')2 fragment, and a Fv fragment.

9. A method for delivering a cargo to a cell, said method comprising contacting said cell with a composition of claim 1 wherein said targeting moiety binds said cell, thereby delivering the cargo to said cell.

10. The method of claim 9, wherein said cargo is delivered to the cytosol or intracellular compartments of said cell.

11. The method of claim 9, wherein said cell is a mammalian cell.

12. A composition comprising a DNA dendrimer, a polypeptide which binds to a cell surface molecule, a biologically active agent, and polyethylene glycol (PEG).

13. A pharmaceutical composition comprising a DNA dendrimer, a polypeptide which binds to a cell surface molecule, a biologically active agent and a pharmaceutically acceptable carrier.

14. The pharmaceutical composition of claim 13, further comprising polyethylene glycol (PEG).

15. A composition consisting essentially of
   a DNA dendrimer,
   a cargo which is a biologically active agent,
   and a targeting moiety which is a polypeptide which binds to a cell surface molecule,
   wherein said composition provides intracellular delivery of the cargo.

* * * * *